United States Patent
Kinouchi et al.

(10) Patent No.: US 8,355,043 B2
(45) Date of Patent: Jan. 15, 2013

(54) MEDICAL APPARATUS

(75) Inventors: Hideaki Kinouchi, Hachioji (JP);
Tsutomu Urakawa, Hachioji (JP);
Junichi Ohnishi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/227,773

(22) Filed: Sep. 8, 2011

(65) Prior Publication Data
US 2012/0062717 A1    Mar. 15, 2012

Related U.S. Application Data

(63) Continuation of application No. PCT/JP2011/058317, filed on Mar. 31, 2011.

(30) Foreign Application Priority Data

May 10, 2010 (JP) .................................. 2010-108425

(51) Int. Cl.
*H04N 7/12* (2006.01)

(52) U.S. Cl. ......................................................... 348/74

(58) Field of Classification Search .............. 348/47–50; H04N 7/12
See application file for complete search history.

(56) References Cited

U.S. PATENT DOCUMENTS

| | | | | |
|---|---|---|---|---|
| 6,930,705 | B2 * | 8/2005 | Tanaka ............................. | 348/45 |
| 7,666,181 | B2 * | 2/2010 | Abou El Kheir ................. | 606/1 |
| 8,182,414 | B2 * | 5/2012 | Handa et al. ................... | 600/102 |
| 2006/0184160 | A1 | 8/2006 | Ozaki et al. | |
| 2007/0165932 | A1 | 7/2007 | Nishimura et al. | |
| 2007/0197865 | A1 | 8/2007 | Miyake et al. | |
| 2008/0309758 | A1 * | 12/2008 | Karasawa et al. ............... | 348/65 |
| 2008/0312500 | A1 | 12/2008 | Asada et al. | |

FOREIGN PATENT DOCUMENTS

| | | |
|---|---|---|
| EP | 1 618 828 A1 | 1/2006 |
| EP | 1 691 312 A2 | 8/2006 |
| EP | 1 902 664 A1 | 3/2008 |
| EP | 2 085 019 A1 | 8/2009 |
| JP | 10-314104 | 12/1998 |
| JP | 2005-319086 | 11/2005 |
| JP | 2006-223375 | 8/2006 |
| JP | 2006-320650 | 11/2006 |
| JP | 2007-222238 | 9/2007 |
| JP | 2008-307226 | 12/2008 |
| WO | WO 98/11815 A1 | 3/1998 |

OTHER PUBLICATIONS

European Search Report dated Feb. 29, 2012 from corresponding European Patent Application No. EP. 11 78 0446.8.

* cited by examiner

*Primary Examiner* — Tung Vo

(74) *Attorney, Agent, or Firm* — Scully Scott Murphy & Presser, PC

(57) ABSTRACT

A medical apparatus includes: a first image pickup section that is fixed to a body wall and picks up an image of an inside of a body cavity; a recording section that records in advance, in preparation for a case in which a predetermined image change occurs in a first image picked up by the first image pickup section, a predetermined image area in the first image or a coordinate for specifying the predetermined image area; and a display section that displays, when the predetermined image change occurs in the first image, the image area or the coordinate recorded in the recording section to be superimposed on the first image picked up by the first image pickup section.

18 Claims, 15 Drawing Sheets

OVERHEAD IMAGE

MAIN IMAGE

OVERHEAD IMAGE

MAIN IMAGE

OVERHEAD IMAGE

MAIN IMAGE

MAIN IMAGE

OVERHEAD IMAGE

MAIN IMAGE

OVERHEAD IMAGE

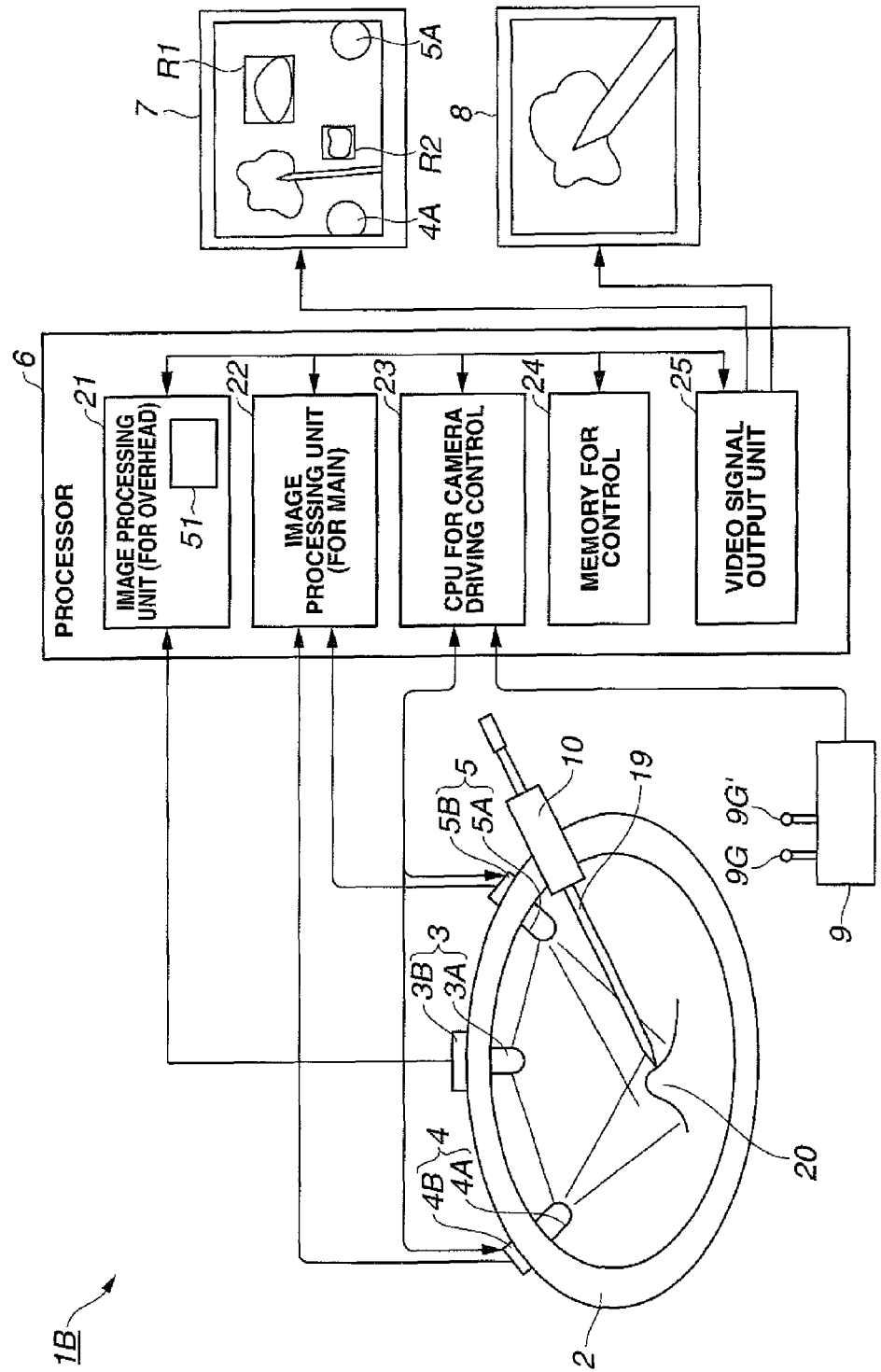

OVERHEAD IMAGE          MAIN IMAGE

OVERLAPPING RANGE

OVERLAPPING RANGE

MEDICAL APPARATUS

CROSS REFERENCE TO RELATED APPLICATION

This application is a continuation application of PCT/JP2011/058317 filed on Mar. 31, 2011 and claims benefit of Japanese Application No. 2010-108425 filed in Japan on May 10, 2010, the entire contents of which are incorporated herein by this reference.

BACKGROUND OF THE INVENTION

1. Field of the Invention

The present invention relates to a medical apparatus for picking up an image of an inside of a body with image pickup means and performing a surgical operation and the like.

2. Description of the Related Art

In recent years, a medical apparatus by an endoscope apparatus for inserting an endoscope into a body and performing a surgical operation such as excision of a lesion part under an observation of the endoscope is widely used.

For example, when a surgical operation inside an abdominal cavity is performed, it is a widely performed practice to insert, without making a surgical incision in an abdomen, an endoscope into an insertion hole by a trocar and perform a surgical operation such as excision or the like of a lesion with a treatment instrument or the like under an observation of an endoscope.

To make it easy to perform the surgical operation under the endoscope observation in this way, in Japanese Patent Application Laid-Open Publication No. 2008-307226 as a first related art, an endoscope system is disclosed including a camera that performs image pickup in a body cavity, a camera side magnet and a magnet for fixing that are connected to the camera and hold an abdominal wall using different surfaces of the abdominal wall and fix the camera in the body cavity, and a camera control unit that performs control of the camera.

In Japanese Patent Application Laid-Open Publication No. 2005-319086 as a second related art, an intra-body cavity observation system is disclosed that fixes an observation unit including an LED, a battery, an observation optical system, and a video signal transmitting section on a body wall and transmits a video signal of an intra-body cavity video picked up by the observation optical system of the observation unit to a video signal processing machine on a monitor side by radio with the video signal transmitting section.

In Japanese Patent Application Laid-Open Publication No. 2006-320650 as a third related art, an image display apparatus is disclosed including an image processing control section that acquires an image from a recording section, controls various kinds of image processing applied to the acquired image, and causes the recording section to record images of processing results, an image classifying section that calculates correlation values of images continuing in time series and classifies the images into image groups according to the calculated correlation values, an image-of-attention detecting section that detects characteristic image areas having predetermined characteristics from the images and detects characteristic images having the detected characteristic image areas as images of attention, a representative image extracting section that extracts the images of attention and top images in the image groups as representative images and sets a display rate for the extracted representative images, and an image display control section that performs control for sequentially displaying a series of representative images according to the set display rate.

The third related art discloses that the image-of-attention detecting section determines whether a bleeding region is present according to image processing in accumulated past images and the image processing control section records, and when a bleeding region is present, position information of the bleeding region in the image recording section.

SUMMARY OF THE INVENTION

A medical apparatus according to an aspect of the present invention includes: a first image pickup section that is fixed to a body wall and picks up an image of an inside of a body cavity; a recording section that records in advance, in preparation for a case in which a predetermined image change occurs in a first image picked up by the first image pickup section, a predetermined image area in the first image or a coordinate for specifying the predetermined image area; and a display section that displays, when the predetermined image change occurs in the first image, the image area or the coordinate recorded in the recording section to be superimposed on the first image picked up by the first image pickup section.

BRIEF DESCRIPTION OF THE DRAWINGS

FIG. 13A is an overall configuration diagram of a medical apparatus according to a modification of the first embodiment of the present invention;

FIG. 19B is a diagram of an enlarged image example displayed on the overhead monitor or the like;

DETAILED DESCRIPTION OF THE PREFERRED EMBODIMENTS

Embodiments of the present invention are explained below with reference to the drawings.

First Embodiment

Figure 1:
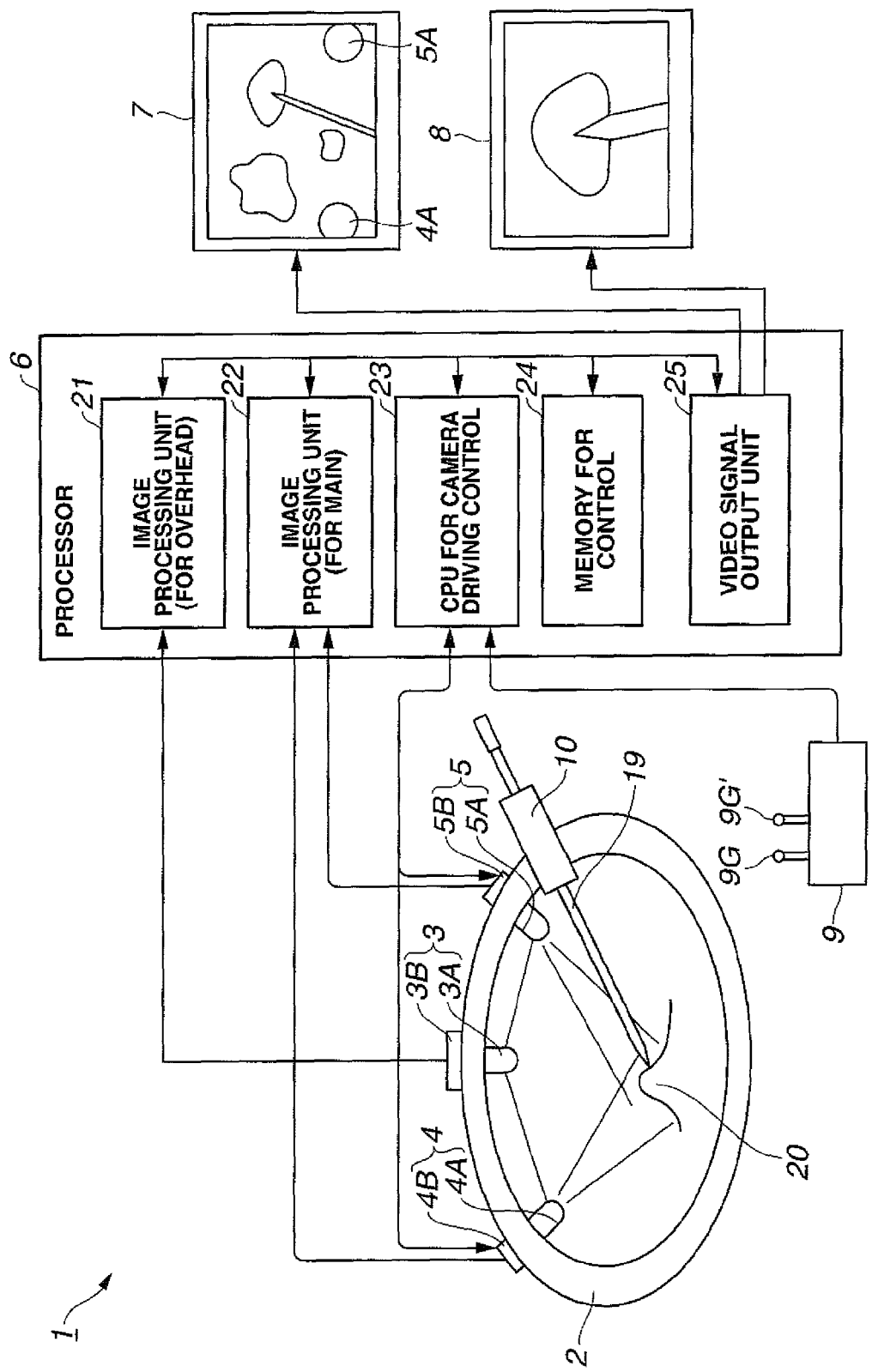
FIG. 1 is a configuration diagram showing an overall configuration of a medical system including a first embodiment of the present invention.

As shown in FIG. 1, a medical apparatus 1 according to a first embodiment of the present invention includes an overhead camera section 3 that picks up an image of an inside of an abdominal cavity at a wide angle and a first main camera section 4 and a second main camera section 5 that pick up images of the inside of the abdominal cavity at narrower angles (compared with the overhead camera section 3), the overhead camera section 3, the first main camera section 4, and the second main camera section 5 being fixed to an abdominal wall of an abdomen 2 of a patient.

The medical apparatus 1 includes a processor 6 that performs image processing and the like for the overhead camera section 3, the main camera sections 4 and 5, an overhead monitor 7 that displays an image picked up by the overhead camera section 3 (referred to as overhead image), and a main monitor 8 that displays images picked up by the main camera sections 4 and 5 (referred to as main images).

The medical apparatus 1 includes a camera operation interface (abbreviated as camera operation I/F) 9 with which a surgeon performs recording of the images picked up by the overhead camera section 3 and the main camera sections 4 and 5 and instruction operation for, for example, movement of image pickup positions and image pickup directions of the main camera sections 4 and 5 to desired places.

In an example explained in this embodiment, the overhead camera section 3 and the main camera sections 4 and 5 respectively include an overhead camera 3A as first image pickup means and main cameras 4A and 5A as second image pickup means arranged on an inside of an abdomen 2 and a receiving unit 3B and transmitting and receiving units 4B and 5B arranged on an outside of the abdomen 2.

This embodiment is not limited to such a configuration for transmitting a signal by radio but may be a configuration (e.g., a configuration shown in FIG. 14) for extending signal lines respectively from the overhead camera 3A and the main cameras 4A and 5A to connect the overhead camera 3A and the main cameras 4A and 5A to the processor 6 and performing signal transmission by wire.

When the configuration for performing the signal transmission by wire is adopted, the receiving unit 3B and the transmitting and receiving units 4B and 5B are unnecessary. In this embodiment, the configuration including the two main cameras 4A and 5A as the second image pickup means is shown.

By adopting the configuration including the two main cameras 4A and 5A, for example, a state in which a lesion part is treated by a treatment instrument can be more surely grasped or recognized than in a case in which one main camera is provided. In the case of one main camera, a picked-up image from one direction is obtained. On the other hand, in the case of two main cameras, picked-up images from different two directions are obtained. Therefore, a state of the treatment instrument can be grasped or recognized in more detail. A state of the lesion part can also be grasped or recognized in more detail.

However, this embodiment is not limited to the case in which two main cameras are provided but can also be applied to a case in which three or more main cameras are provided or one main camera is provided.

Operation for fixing the overhead camera 3A and the main cameras 4A and 5A on an inside of the abdomen 2 as shown in FIG. 1 can be performed by using a not-shown endoscope or the like in a puncture hole formed in the abdomen 2 using a trocar 10 by a method disclosed in, for example, Japanese Patent Application Laid-Open Publication No. 2008-307226.

A side of the overhead camera 3A and the main cameras 4A and 5A and a side of the receiving unit 3B and the transmitting and receiving units 4B and 5B can be detachably fixed, for example, in a state in which an abdominal wall is held by magnetic force using magnets but may be fixed by other fixing means such as an adhesive.

In FIG. 1, a state in which, after the overhead camera 3A and the main cameras 4A and 5A are fixed on the inside of the abdomen 2, a treatment instrument 19 is inserted through the trocar 10 and treatment is applied to a region (referred to as place) of a treatment target.

Figure 2:
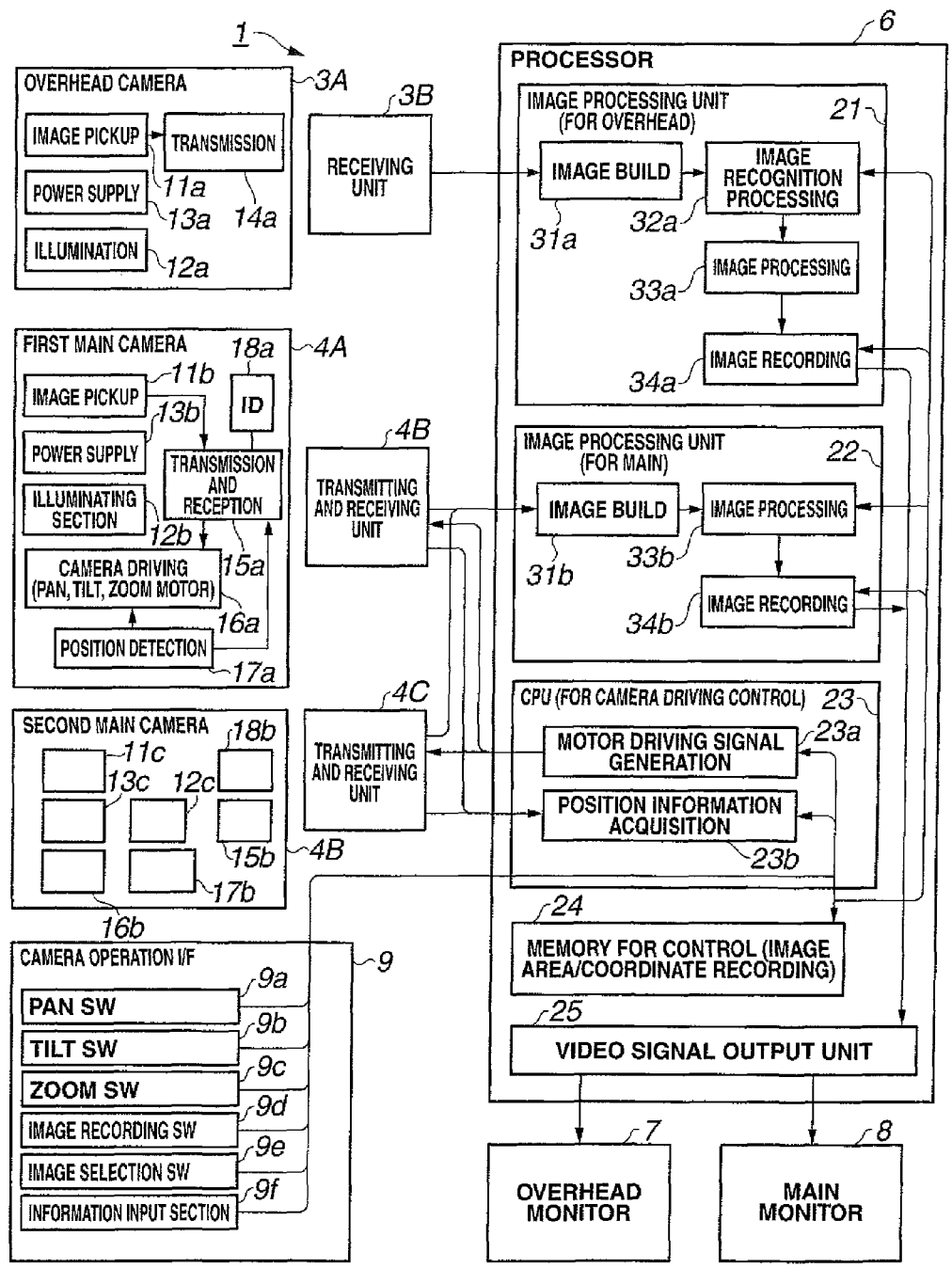
FIG. 2 is a block diagram showing an internal configuration in a medical apparatus shown in FIG. 1.

In the overhead camera 3A and the main cameras 4A and 5A, as shown in FIG. 2, image pickup units 11a to 11c including an image pickup function, illuminating units 12a to 12c that illuminate a portion where image pickup is performed, and power supply units 13a to 13c including batteries for supplying electric power to the image pickup units 11a to 11c and the like are respectively housed in armor containers having, for example, a substantially cylindrical shape.

The overhead camera 3A incorporates a transmitting unit 14a and transmits by radio, with the transmitting unit 14a, an image signal of an overhead image as a picked-up image picked up by the image pickup unit 11a. The receiving unit 3B receives the image signal transmitted by the transmitting unit 14a and outputs the image signal to an image processing unit (for overhead) 21 in the processor 6.

The main cameras 4A and 5A further incorporate transmitting and receiving units 15b and 15c, camera driving units 16a and 16b, position detecting units 17a and 17b, and identification information generating units (in the figure, abbreviated as ID) 18a and 18b.

The second main camera 5A has the same configuration as that of the first main camera 4A except that identification information generated by the identification information generating unit 18b is different. In FIG. 2, an internal configuration is schematically shown.

The main cameras 4A and 5A transmit image signals of main images as picked-up images respectively picked up by the image pickup units 11b and 11c by radio via the transmitting and receiving units 15a and 15b (transmitting sections inside). The transmitting and receiving units 4B and 5B (receiving sections inside) receive the transmitted image signals and output the image signals to an image processing unit (for main) 22 in the processor 6.

In transmitting the image signals, the transmitting and receiving units 15a and 15b transmit the image signals with identification information attached thereto. The image processing unit (for main) 22 performs management of a main image according to the identification information.

Compared with the configuration of the overhead camera 3A explained above, the main cameras 4A and 5A further include camera driving units 16a and 16b for moving a place whose image is picked up, and position detecting units 17a and 17b that detect driving information (also referred to as setting information) of the camera driving units 16a and 16b that pick up images of the place.

The overhead camera 3A has a wide-angle observation field of view (e.g., an observation field of view close to 180°). In a state in which the overhead camera 3A is fixed to an abdominal wall, the observation field of view of the overhead camera 3A is an overhead image obtained by picking up an inside of an abdominal cavity in a wide range in a view angle state of a wide angle. In a surgical operation, the overhead camera 3A is used in a view angle state of a fixed wide angle.

As schematically shown in FIG. 1, in an overhead image, main camera images (simplified as indicated by 4A and 5A) obtained by picking up images with the main cameras 4A and 5A in observation fields of view thereof are displayed.

On the other hand, the main cameras 4A and 5A have a narrower observation field of view (a narrower angle) compared with the overhead camera 3A and can move and set an observation field of view (an image pickup range) with the camera driving units 16a and 16b as explained below.

The main cameras 4A and 5A can be set in a desired observation field of view in a driving range of the camera driving units 16a and 16b in the abdominal cavity and can be set to a proper image size by the camera driving units 16a and 16b. Therefore, the surgeon can perform observation in detail. FIG. 1 shows a display example of, for example, a main image by one main camera 5A.

In this embodiment, the surgeon can survey (look out over) the inside of the abdominal cavity at a wide angle using an overhead image and can observe in detail an arbitrary position with the two main cameras 4A and 5A.

This makes it unnecessary to post a scopist (an endoscope holder) who sets and holds a scope (an endoscope) in a field of view in which a place to be treated can be observed by the scope in the related art. Therefore, since the scopist who occupies a place near the surgeon is not present, the surgeon has an advantage that the surgeon can easily perform a surgical operation without being limited by the place occupied by the scopist.

The camera driving units 16a and 16b include a pan (swinging in a left/right direction) function and a tilt (tilting in an up/down direction) function for the image pickup units 11b and 11c and the illuminating units 12b and 12c and also include a zoom function for enabling enlarged observation by the image pickup units 11b and 11c.

In other words, the camera driving units 16a and 16b can move and set the image pickup units 11b and 11c as image pickup means by panning and tilting the same such that the image pickup units 11b and 11c can pick up images of a desired position. The camera driving units 16a and 16b can change, with the zoom function, an angle of view for image pickup, for example, increase image pickup magnification to be larger than that in the case of the overhead camera 3A, and set the image pickup units 11b and 11c in a state in which a lesion of attention or the like can be observed in detail.

Setting information of pan, tilt, and zoom by the camera driving units 16a and 16b (in other words, information concerning image pickup positions of the image pickup units 11b and 11c, information concerning an image pickup direction, and zoom information of an angle of view of image pickup) is detected by the position detecting units 17a and 17b included in information acquiring means.

The setting information of the camera driving units 16a and 16b detected by the position detecting units 17a and 17b is recorded in the memory for control 24 as history information together with, for example, a place whose image is picked up by image recording operation by the surgeon (e.g., together with time of instruction operation for a recorded image).

The surgeon operates a pan SW 9a, a tilt SW 9b, and a zoom SW 9c provided in the camera operation I/F 9, whereby instruction signals for pan, tilt, and zoom are outputted to a CPU for camera driving control (simply abbreviated as CPU) 23 on the inside of the processor 6. The CPU 23 performs control of the processor 6, the overhead camera 3A, the main cameras 4A and 5A, and the camera operation I/F 9 included in the medical apparatus 1.

The CPU 23 generates, with a motor driving signal generating section 23a, motor driving signals corresponding to the instruction signals for pan, tilt, and zoom and performs control for driving the camera driving unit 16a or 16b of the main camera 4A or 5A via the transmitting and receiving unit 4B or 4C. The main camera 4A or 5A is set in a state in which the main camera 4A or 5A picks up an image of a place corresponding to the instruction signals.

In other words, the camera driving unit 16a or 16b of the main camera 4A or 5A changes to a (image pickup) setting state for picking up an image of a target place instructed by the surgeon using the camera operation I/F 9.

When the camera driving unit 16a or 16b is driven, setting information set to pick up an image of a predetermined place by the driving is detected by the position detecting unit 17a or 17b. A detection signal of the detection is outputted to the position information acquiring section 23b via the transmitting and receiving unit 15a or 15b or the transmitting and receiving unit 4B or 5B.

The position information acquiring section 23b acquires setting values of pan, tilt, and zoom, in other words, (setting information including) information concerning image pickup positions and image pickup directions and zoom information of the main cameras 4A and 5A from detection signals of pan, tilt, and zoom by the position detecting units 17a and 17b.

When instruction operation for image recording is performed by the surgeon, the position information acquiring section 23b records (stores) the setting information of the camera driving units 16a and 16b in the memory for control 24 in time series. The setting information may be recorded in a recording section such as a memory of the position information acquiring section 23b instead of the memory for control 24.

In the camera operation I/F 9, an image recording SW 9d for performing recording instruction operation for an image and an image selection SW 9e for performing image selection for selecting which of main images respectively picked up by the two main cameras 4A and 5A is displayed on the main monitor 8 are provided and an information input section 9ƒ that inputs information is provided according to necessity.

The camera operation I/F 9 may be configured to be used in common for the main camera 4A and the main camera 5A as shown in FIG. 2. In this case, a not-shown selection switch for designating (selecting) the main camera 4A and the main camera 5A is provided. As the camera operation I/F 9, a (first) camera operation I/F 9G and a (second) camera operation I/F 9G' for performing operation of pan, tilt, and zoom independently for the main cameras 4A and 5A respectively may be provided as shown in FIG. 1.

The surgeon can record an overhead image of the overhead camera 3A and main images of the main cameras 4A and 5A by operating the image recording SW 9d.

After setting a state for picking up an image of a place about to be treated by the main cameras 4A and 5A as explained later with reference to FIG. 3, in a state in which a distal end of a treatment instrument is set in the place, the surgeon performs the recording operation by the image recording SW 9d. Consequently, the surgeon can record an overhead image and information concerning image pickup position, image pickup directions, and the like of picked-up images of the main cameras 4A and 5A in the overhead image in association with each other (to correspond to each other).

As explained above, in this embodiment, as one of characteristics, when instruction operation for image recording is performed by the surgeon via the image recording SW 9d, the processor 6 includes the memory for control 24 as recording means (for history information) for recording, for example, in time series, (information concerning) a place, images of which are picked up by the main cameras 4A and 5A, in an overhead image and image pickup position information and image pickup direction information (i.e., image pickup means setting information) of the main cameras 4A and 5A, which pick up images of the place, in association with each other (to correspond to each other).

The place (the information concerning the place) in this case may be a coordinate (or, for example, place specifying means shown in FIG. 7 similar to the coordinate) for specifying the place, may be an image area of a place whose image is picked up, or may be a coordinate for specifying the image area. In other words, the (information concerning) the place only has to be information related to the place.

The overhead image by the overhead camera 3A and the picked-up images of the main cameras 4A and 5A are recorded in time series in association with the place of the image pickup by the main cameras 4A and 5A in the overhead image and a number associated with the place.

In this case, the overhead image is recorded in an image recording section 34a in the image processing unit 21 explained below and the main images are recorded in an image recording section 34b in the image processing unit 22. However, the overhead image and the main images may be recorded in other recording means, for example, the memory for control 24.

Figure 4:
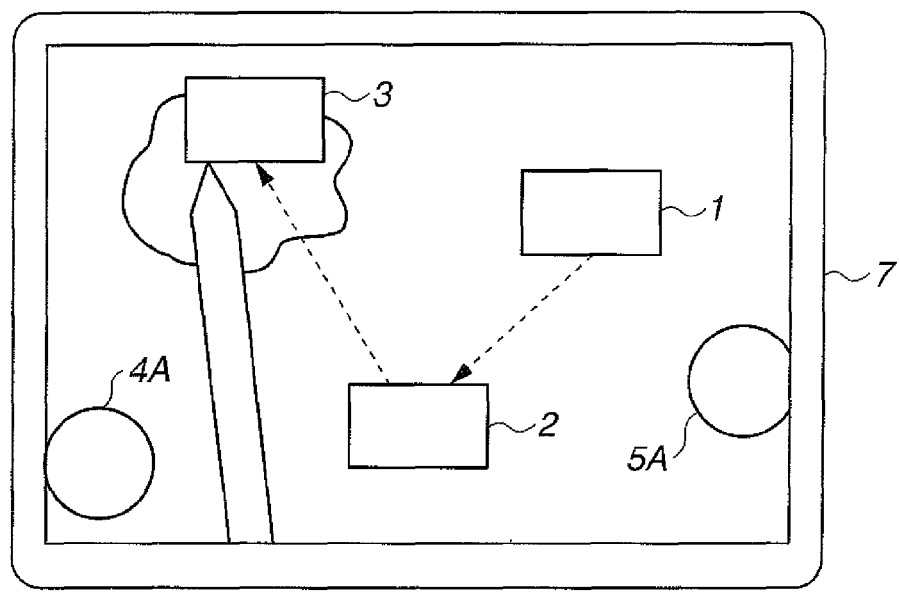
FIG. 4 is an explanatory diagram of an operation by display on an overhead monitor.

The surgeon can display, for example, a place of image pickup by the main cameras 4A and 5A in a present overhead image with a number affixed to the place by performing, for example, instruction operation for displaying history information (or history) from the information input section 9ƒ (explained later with reference to FIG. 4).

The processor 6 includes a video signal output unit 25 connected to the image processing units 21 and 22. The video signal output unit 25 converts image data of an overhead image and main images picked up by the overhead camera 3A and the main camera 4A or 5A and temporarily stored in frame memories for image storage of the image processing units 21 and 22 into video signals of an analog RGB, NTSC/PAL, or IEEE1394 system or the like and output the video signals respectively to the overhead monitor 7 and the main monitor 8.

As shown in FIG. 2, the image processing unit 21 includes an image building section 31a that performs image processing for an image pickup signal (of an overhead image) picked up by the image pickup unit 11a inputted via the receiving unit 3B and builds an overhead image and an image recognition processing section 32a that applies, for example, processing for recognizing a distal end position of the treatment instrument or a place near the distal end position as an image to the overhead image.

The image processing unit 21 includes an image processing section 33a that performs image processing for superimposing, on the place recognized as the image by the image recognition processing section 32a, a number for specifying the place and an image recording section 34a including a frame memory or the like that records an image image-processed by the image processing section 33a.

When an overhead image is recorded in the image recording section 34a (or the memory for control 24), an overhead image generated by the image building section 31a and information concerning a place superimposed on the overhead image and a number may be recorded in association with each other.

When an image is recorded in this way, since information concerning a treated place or the like is recorded in association with the image, it is possible to easily display information concerning a place and a number in the past to be superimposed on an overhead image picked up temporally later and easily display information concerning plural places treated and recorded in the past and numbers to be superimposed on the overhead image.

The image recording section 34a also includes a function of temporarily recording an overhead image to be displayed as a moving image besides an overhead image for which the instruction operation for image recording is performed by the image recording SW 9d. The overhead image temporarily recorded in the image recording section 34a or the like is displayed on the overhead monitor 7 through the video signal output unit 25.

As explained with reference to FIG. 7 and the like, the image recognition processing section 32a performs image recognition processing for setting, for example, a distal end portion of the treatment instrument 19 in a place, images of which are picked up by the main cameras 4A and 5A, in an overhead image and specifying the place, images of which are picked up by the main cameras 4A and 5A, on the overhead image.

The image recognition processing in this case is used to mean both a case in which the processor 6 side subjectively performs image processing for image recognition and a case in which the surgeon as a subject manually performs instruction operation for image recognition (in this case, the processor 6 performs supplementary processing). The image recognition processing may include one of the cases.

After the processing for specifying the place, images of which are picked up by the main cameras 4A and 5A, in the overhead image, the surgeon performs the instruction operation for image recording, whereby, in association with the place specified in the overhead image and a number, setting information of the image pickup of the place by the main cameras 4A and 5A is recorded in the memory for control 24.

In this way, the main cameras 4A and 5A move the places, images of which are picked up by the main cameras 4A and 5A, in the overhead image and the setting information of the place, images of which are also picked up by the main cameras 4A and 5A, in the overhead image in places to which the main cameras 4A and 5A move is recorded in association with each other in time series. The information is history information. The places can be specified by, for example, numbers.

In this embodiment, when bleeding or a state close to bleeding, in a broader sense, a predetermined change occurs or the surgeon recognizes the predetermined change from the overhead image in a place already treated, instruction operation can be performed to number places on the overhead image using the history information and superimpose and display the places.

The surgeon performs selection of numbers associated with plural places displayed on the overhead image, whereby the CPU 23 subjects the main cameras 4A and 5A to movement control with the camera driving units 16a and 16b referring to setting information of the places of the numbers and displays main images picked up by the moved and set main cameras 4A and 5A on the main monitor 8. The surgeon can quickly check a state of bleeding in more detail from the main images.

The memory for control 24 forms recording means for storing in advance, in preparation for a case in which a predetermined change such as bleeding occurs in a treated place, in other words, an overhead image, an image area or a coordinate of a place where such a predetermined change is likely to occur.

The image processing unit 22 includes an image building section 31b that performs image processing for an image pickup signal (of a main image) picked up by the image pickup unit 11b inputted via the transmitting and receiving unit 4B and builds a main image, an image processing section 33b that performs image processing for superimposing a place and a number for specifying the main image on the main image built by the image building section 31b, and an image recording section 34b including a frame memory and the like that records an image subjected to the image processing by the image processing section 33b.

As explained above, in this embodiment, when the image recording SW 9d is operated when treatment is applied to places to be respectively treatment targets in an abdominal cavity, setting information such as image pickup positions in which the places to be treatment targets are set as an observation field of view (an image pickup field of view) by the main cameras 4A and 5A is recorded in the memory for control 24 in time series. In this case, information such as the image pickup positions and the main images are recorded in association with each other.

Therefore, as explained above, the memory for control 24 forms recording means for recording information such as image pickup positions by the main cameras 4A and 5A in the past as history information.

As explained with reference to FIG. 3, when instruction operation for history display is performed by the surgeon from, for example, the information input section 9f, the CPU 23 performs control to read out information concerning places and numbers from the history information stored in the memory for control 24 included in the recording means and display the numbers to be superimposed on the places in the overhead image.

In other words, the CPU 23 has a function of display control means for performing display control for displaying a place recorded in the recording means, i.e., an image area or a coordinate to be superimposed on an overhead image picked up by the overhead camera 3A functioning as the first image pickup means.

The overhead monitor 7 on which the place recorded in the recording means, in other words, the image area or the coordinate is displayed to be superimposed on the overhead image according to the display control by the display control means forms display means subjected to the display control by the display control means.

When a specific number is selected by the surgeon from numbers in the past superimposed and displayed on the overhead monitor 7, the CPU 23 performs control to read out setting information of the main cameras 4A and 5A recorded in association with a place of the number from the memory for control 24 and drive the camera driving units 16a and 16b to cause the main cameras 4A and 5A to pick up images of the place of the selected number.

Therefore, the CPU 23 configures movement control means for subjecting, on the basis of setting information such as an image pickup position and an image pickup direction from the memory for control 24, with the camera driving units 16a and 16b, the main cameras 4A and 5A included in the second image pickup means to movement control to pick up the selected place. A configuration including the CPU 23 and the camera driving units 16a and 16b may be regarded as the movement control means.

The movement control means also includes a function of increasing zoom magnification by the main cameras 4A and 5A to increase image pickup magnification.

The surgeon selects a specific number as explained above, whereby, under the control by the CPU 23, the main cameras 4A and 5A are quickly moved to pick up images of a place of the selected number by the camera driving units 16a and 16b.

A main image picked up by the main camera 4A or 5A is displayed on the main monitor 8.

Therefore, the surgeon checks bleeding or a state close to bleeding in an overhead image. When it is necessary to check the state in more detail, the surgeon can check the state quickly and in detail with simple operation using main images by the main cameras 4A and 5A.

The medical apparatus 1 according to this embodiment includes the first image pickup means including, for example, the overhead camera 3A that is fixed to a body wall and picks up an image of an inside of a body cavity, the recording means including, for example, the memory for control 24 that records in advance, in preparation for a case in which a predetermined change occurs, for example, in a first image as an overhead image picked up by the first image pickup means, a predetermined image area in the first image or a coordinate for specifying the predetermined image area, and the display means including, for example, the overhead monitor 7 that displays, in a case in which predetermined change occurs in the first image, the image area or the coordinate recorded by the recording means to be superimposed on the first image picked up by the first pickup means.

Representative operations of this embodiment are explained with reference to FIG. 3.

Figure 3:
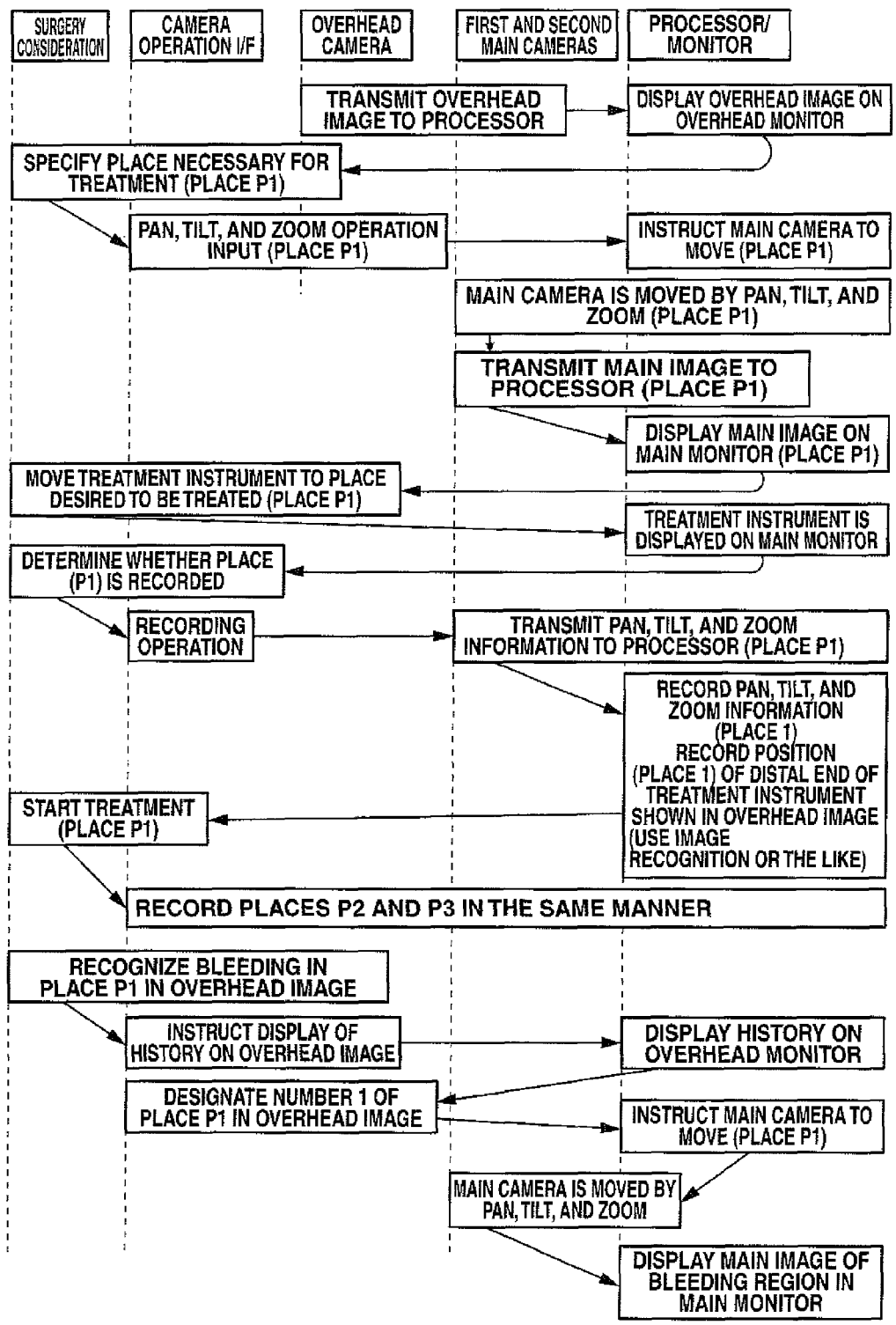
FIG. 3 is an explanatory diagram of representative operations in the first embodiment.

FIG. 3 shows main operations of the surgeon, the camera operation I/F 9, the overhead camera 3A, the first and second main cameras 4A and 5A, and the processor 6/(the overhead monitor 7 and the main monitor 8). In this case, an up to down vertical direction indicates elapse of time.

As shown in FIG. 1, the surgeon fixes the overhead camera 3A and the main cameras 4A and 5A in the abdominal wall of the abdomen 2. Then, as shown in FIG. 3, the overhead camera 3A transmits a picked-up overhead image to the processor 6. The processor 6 displays the overhead image on the overhead monitor 7.

The surgeon observes the overhead image and specifies a place necessary for treatment. The place is represented as place P1. The surgeon operates the camera operation I/F 9 such that images of the place P1 can be picked up by the main cameras 4A and 5A.

In other words, the surgeon operates the pan SW 9a, the tilt SW 9b, and the zoom SW 9c of the camera operation I/F 9. Then, an operation signal of the camera operation I/F 9 is sent to the CPU 23. The CPU 23 performs movement instruction to instruct the main cameras 4A and 5A to pick up images of the place P1.

Specifically, according to operation of the pan SW 9a, the tilt SW 9b, and the zoom SW 9c, the CPU 23 drives the camera driving units 16a and 16b. The image pickup units 11b and 11c of the main cameras 4A and 5A move (image pickup positions and directions) to pick up images of the place P1. A main image set in a state for picking up in detail, at a proper angle of view, the images of the place P1 picked up by the main cameras 4A and 5A is transmitted to the processor 6.

A main image obtained by picking up an image of the place P1 is displayed on the main monitor 8.

In order to perform treatment using a treatment instrument in the place P1 while observing the overhead image and the main image, the surgeon inserts the treatment instrument 19 into an abdominal cavity via the trocar 10. The surgeon moves the distal end portion of the treatment instrument 19 to the place P1 that the surgeon desires to treat while looking at the treatment instrument 19 inserted in the abdominal cavity in the overhead image.

Then, a distal end side of the treatment instrument 19 is displayed on the main monitor 8, on which the place P1 is displayed in detail, together with the place P1 about to be treated. A main image on the main monitor 8 shown in FIG. 1 indicates a display example in this case.

The surgeon determines whether the place P1 is to be recorded. When the surgeon attempts to perform treatment in this place with the treatment instrument 19, the surgeon performs operation for performing image recording. Specifically, the surgeon operates the image recording SW 9d. According to the operation, pan, tilt, and zoom information (setting information) of the main cameras 4A and 5A is transmitted to the processor 6 together with time (hour) of this recording operation.

In the memory for control 24 in the processor 6, main images of the place P1 picked up by the main cameras 4A and 5A and the pan, tilt, and zoom information, i.e., information concerning image pickup positions and image pickup directions are recorded in association with each other.

In the memory for control 24, a position of the treatment instrument distal end (or an image area) reflected on the overhead image is, for example, subjected to image recognition (including the case of specific operation by the surgeon) and recorded in the memory for control 24 in association with the place P1.

In this case, the surgeon may input a number (e.g., N, N=1) of the recorded place P1 from the information input section 9f or the place P1 may be set to automatically affix a number 1 of an initial value according to switch-on of the information input section 9f such that the place P1 in the overhead image can be easily specified from other places.

Consequently, in the memory for control 24, the place P1 in the recorded overhead image can be specified by the number 1 and the setting information of the main cameras 4A and 5A that pick up images of the place P1 is recorded as history information (in which treated places are recorded in time series) in association with the place P1 and the number 1 of the overhead image. The main images by the main cameras 4A and 5A are also recorded in association with the place P1 and the number 1 (in a state in which identification information is further affixed).

Therefore, as explained below, when the surgeon designates or selects the number 1 of the place P1 and performs operation for a movement instruction, since the setting information of the main cameras 4A and 5A is recorded in association with the number 1, it is possible to quickly move the main cameras 4A and 5A to a state for picking up images of the place P1.

After making it possible to specify the place P1 in this way, as shown in FIG. 3, the surgeon starts treatment for medical treatment using the treatment instrument 19 in the place P1. After performing the treatment in the place P1, the surgeon moves the place and performs the same processing. In performing the processing, in the same manner as the treatment performed in the place P1, in other places P2 and P3 where treatment is necessary, the surgeon records setting information of the main cameras 4A and 5A in association with the places P2 and P3.

Figure 5:
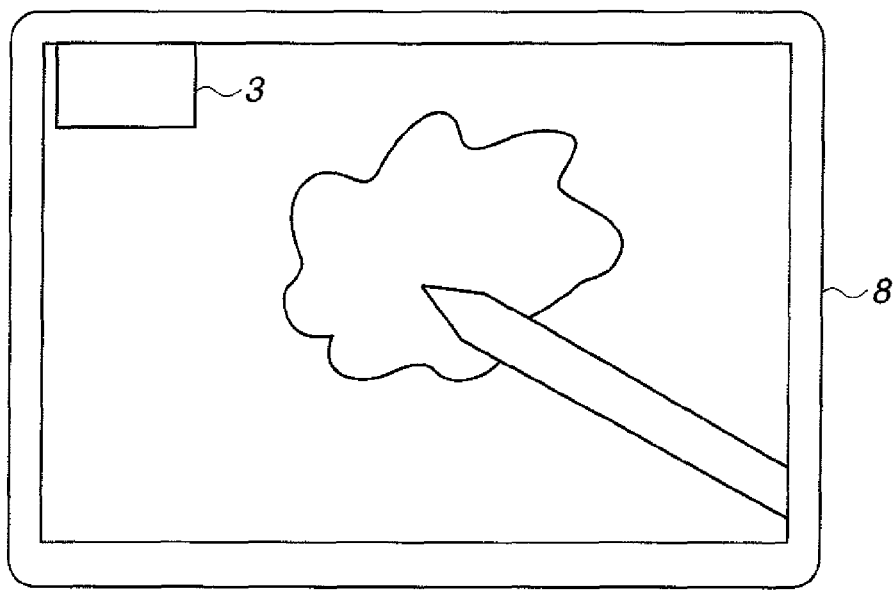
FIG. 5 is a diagram showing a display example on a main monitor.

FIG. 5 shows a main image example displayed on the main monitor 8 while the treatment is performed by the treatment instrument in the place P3. In FIG. 5, a number 3 of the place P3 is displayed on the main monitor 8.

While the treatment is performed by the treatment instrument, for example, in the place P3 in this way, the surgeon could recognize bleeding in the place P1, for example, in a wide-angle overhead image.

Since the overhead image has a wide angle, the surgeon cannot check a state of the bleeding in detail. Therefore, the surgeon performs a display instruction for displaying a history on the overhead image from the information input section 9f. The display instruction is input to the CPU 23. The CPU 23 reads out information recorded in the memory for control 24 and performs a control operation for display of a history corresponding to the information.

On the overhead monitor 7, histories of the places P1 to P3 recorded so far are displayed on the overhead image according to the numbers 1 to 3. FIG. 4 shows a display example of the histories. As shown in FIG. 4, on the overhead image, a number N of a place PN is displayed to be superimposed on the places P1 to P3 recorded in the past. The order of the histories may be displayed as indicated by dotted lines or may be not displayed. Therefore, the surgeon designates (selects) the number 1 from the information input section 9f.

Then, a signal of this designation is input to the CPU 23 of the processor 6. The CPU 23 performs a movement instruction for moving the main cameras 4A and 5A to the place P1 of the number 1.

In the memory for control 24, the setting information of the main cameras 4A and 5A is recorded in association with the place P1 of the number 1. Therefore, the CPU 23 drives the camera driving units 16a and 16b according to the setting information.

Figure 6:
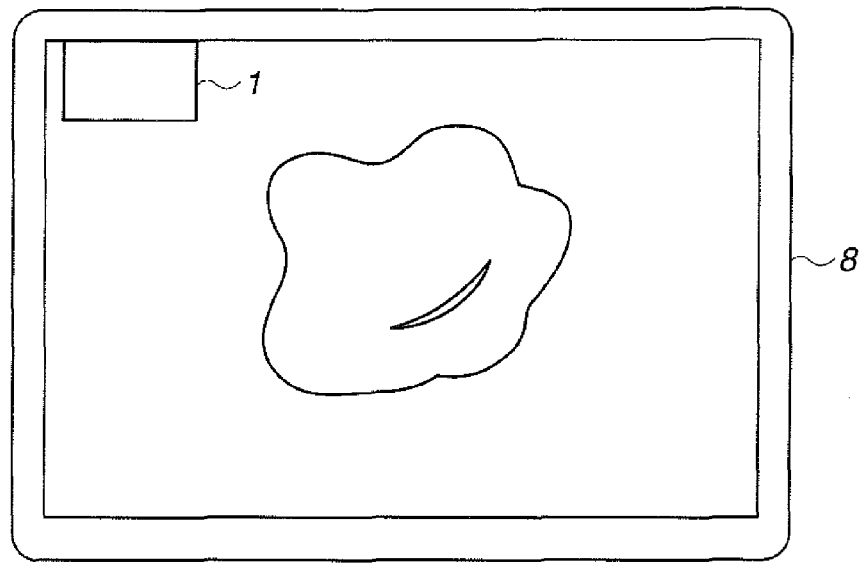
FIG. 6 is a diagram showing a display example of a main image picked up by a main camera after movement moved from a present setting position.

In the main cameras 4A and 5A, the image pickup units 11b and 11c are moved (driven) by pan, tilt, and zoom of the setting information and moved and set in a state for picking up an image of the place P1. A main image picked up by the main camera 4A or 5A is displayed on the main monitor 8. FIG. 6 shows a display example of the main image in this case. The surgeon can check a bleeding state in detail according to the display of the main image on the main monitor 8. The surgeon quickly performs treatment corresponding to the bleeding state according to a detailed check result.

As explained above, in this embodiment, the place PN treated in the past where a predetermined change such as bleeding in the overhead image is likely to occur can be recorded as history information in advance in association with the setting information of the main cameras 4A and 5A that pick up images of the place PN and can be displayed on the display means. Therefore, when the surgeon recognizes a predetermined change such as bleeding in the treated place PN in the overhead image, the surgeon can check the place PN quickly and in detail with simple operation.

Therefore, this embodiment can reduce, when the surgeon performs a surgical operation, operation performed by the surgeon or the like and can provide the medical apparatus 1 with which the surgeon can more smoothly and easily perform the surgical operation.

Figure 8:
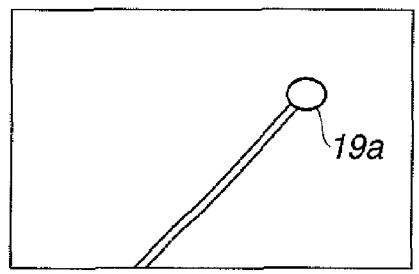
FIG. 8 is an explanatory diagram for specifying an image pickup position by the main camera on an overhead image using a treatment instrument.
Figure 8:
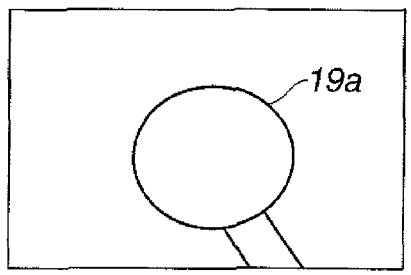
Figure 9:
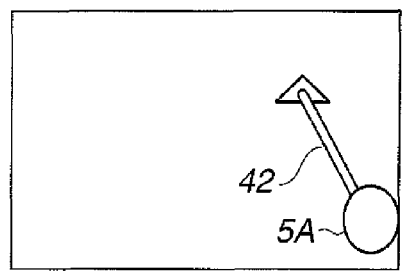
FIG. 9 is an explanatory diagram for specifying an image pickup position by the main camera on an overhead image using light.
Figure 9:
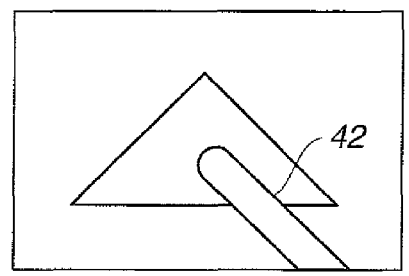
Figure 10:
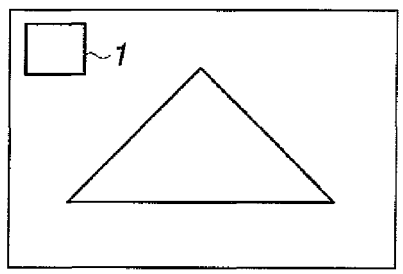
FIG. 10 is an explanatory diagram for specifying an image pickup position by the main camera on an overhead image through image recognition.
Figure 10:
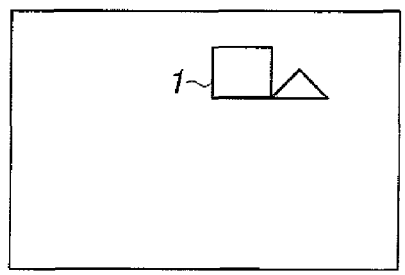
Figure 11:
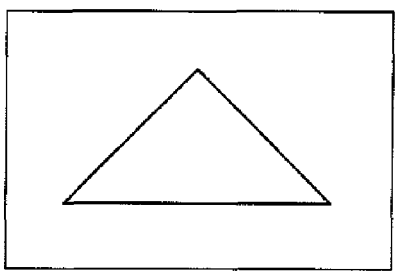
FIG. 11 is an explanatory diagram for specifying an image pickup position by the main camera on an overhead image using information of the main camera reflected on the overhead image.
Figure 11:
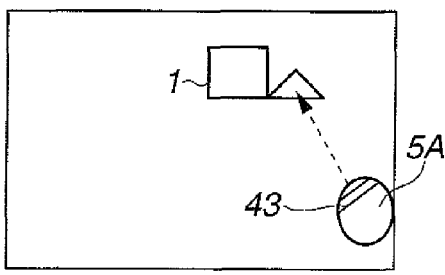

As an image recognition method by the image recognition processing section 32a, various methods can be used as explained below. A left side in FIG. 7 indicates an overhead image and a right side indicates a main image. The same display is shown in FIGS. 8 and 9. In FIGS. 10 and 11, an overhead image and a main image are shown in an opposite arrangement.

Figure 7:
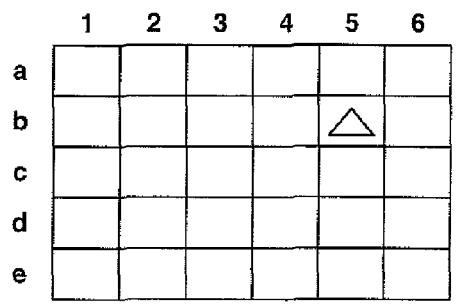
FIG. 7 is an explanatory diagram for specifying an image pickup position by the main camera on an overhead image.
Figure 7:
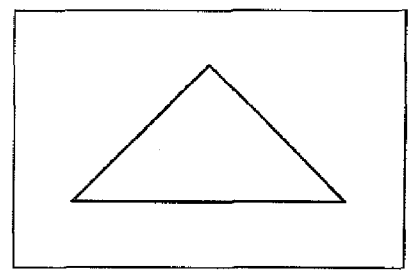

The overhead image shown in FIG. 7 is divided into plural image areas designated (specified) by, for example, (i, j) with horizontal 1 to 6 and vertical a to e. The overhead image is not limited to be divided into such a number of divisions.

The surgeon checks in which image area in the overhead image a display image corresponding to a display image (in FIG. 7, schematically indicated by a triangle) of a main image equivalent to an image pickup place, images of which are picked up by the main cameras 4A and 5A, is present. In an example shown in FIG. 7, the surgeon designates a place of an image area (5, b).

According to the designation, the surgeon specifies (recognizes) that the place of the image area (5, b) in the overhead image is an image pickup coordinate or an image pickup place, images of which are picked up by the main cameras 4A and 5A.

When the place is represented as PN, the setting information of the main cameras 4A and 5A is recorded in the memory for control 24 in association with the place PN and the number N.

FIG. 8 shows a method of specifying an image pickup position of the main cameras 4A and 5A in an overhead image using a reference object such as operation equipment or a treatment instrument. In a main image, only a vicinity of the distal end portion 19a (schematically indicated by a circle) of the treatment instrument is displayed. However, in the overhead image, the treatment instrument is displayed in a wider range.

The surgeon checks where in the overhead image the distal end portion 19a of the treatment instrument in the main image is displayed. In this case, a place may be designated as shown in FIG. 7. Alternatively, a position of the main image in the overhead image, i.e., an image pickup position of the main cameras 4A and 5A may be specified using an edge image obtained by applying edge treatment to the distal end portion 19a.

FIG. 9 shows a method of specifying an image pickup position when a light source for irradiating light such as a laser pointer is provided in the main cameras 4A or 5A. In an overhead image, for example, a portion irradiated by light 42 of the light source is shown together with an image of the main camera 5A.

On the other hand, in a main image, a portion irradiated by the light 42 near a place (schematically indicated by Δ) of which an image is picked up in enlargement by the main camera 5A, is displayed. A wavelength of the light 42 is set to wavelength easily distinguished from intra-body illumination light or a shape of the irradiated light is set to be easily distinguished.

Consequently, the surgeon can easily specify in which position in the overhead image an image pickup position of the main camera 5A is located. In FIGS. 7 to 9, a method in which the surgeon designates an image pickup position of the main cameras 4A and 5A on the overhead image is explained. On the other hand, image recognition for specifying a relative position with an apparatus such as the image recognition processing section 32a on the processor 6 side may be performed as explained below.

FIG. 10 shows a method of recognizing, with the image processing section 33b, a characteristic portion of a place of which an image is picked up, in a main image as an image. The image processing section 33b recognizes, for example, a shape of a distal end portion of a treatment instrument in the place P1 as an image and sets the recognized image as an image of the number 1 in the place P1.

A characteristic of the recognized image is sent to the image recognition processing section 32a. The image recognition processing section 32a finds an image portion having the characteristic from an overhead image. When the image recognition processing section 32a determines that a portion having a correlation equal to or larger than a predetermined value is present in the overhead image, the image recognition processing section 32a automatically marks the place P1 as a place corresponding to the characteristic portion of the main image and automatically marks a number of the place P1 as 1.

FIG. 11 shows an image recognition method for specifying an image pickup position of the main camera 4A or 5A using image information of the main camera 4A or 5A reflected on an overhead image. A mark 43 is affixed to, for example, an armor container of the main camera 5A reflected on the overhead image. When a direction of the image pickup unit 11b changes, the mark 43 also changes.

The image recognition processing section 32a estimates an image pickup position of the main camera 5A from a shape of the armor container of the main camera 5A reflected on the overhead image and information concerning the mark 43. In FIG. 11, a distal end portion of an arrow of a dotted line is estimated as the image pickup position of the main camera 5A. On the assumption that the estimated position in the overhead image is the place P1 where the main image is picked up, the place P1 is automatically marked with the specified number 1.

Besides, position sensors may be respectively provided in the overhead camera 3A and the main cameras 4A and 5A and relative positions in both the images may be specified from detection information of the position sensors.

The overhead camera 3A is in a fixed state, the position sensor may be provided only on the side of the main cameras 4A and 5A.

In the example explained in the embodiment, the overhead image of the overhead camera 3A is displayed on the overhead monitor 7 using the one overhead camera 3A and the two main cameras 4A and 5A and the main image of selected one main camera of the two main cameras 4A and 5A is displayed on the main monitor 8.

Figure 12A:
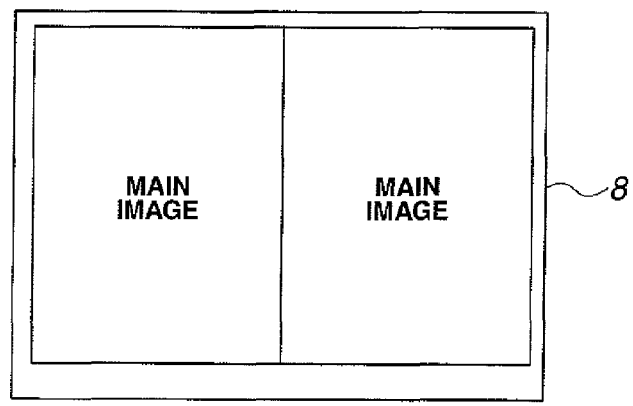
FIG. 12A is a diagram showing a state in which two main images are displayed on the main monitor.

This embodiment is not limited to a case of such a display form. For example, as shown in FIG. 12A, a main image of each of the two main cameras 4A and 5A may be divided into two and displayed on the main monitor 8.

Two main monitors may be provided to display main images of the main cameras 4A and 5A.

Figure 12B:
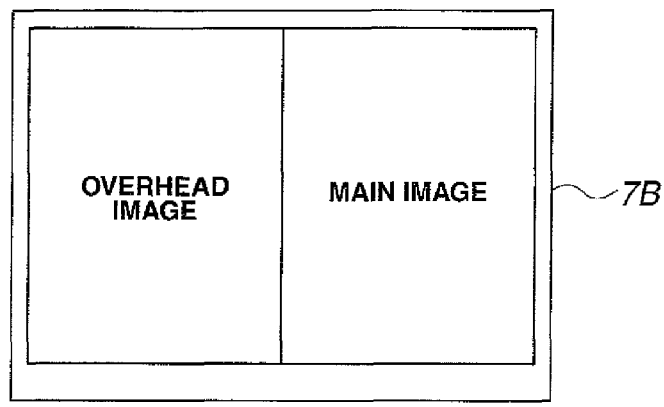
FIG. 12B is a diagram showing a state in which an overhead image and a main image are displayed on one monitor.
Figure 12C:
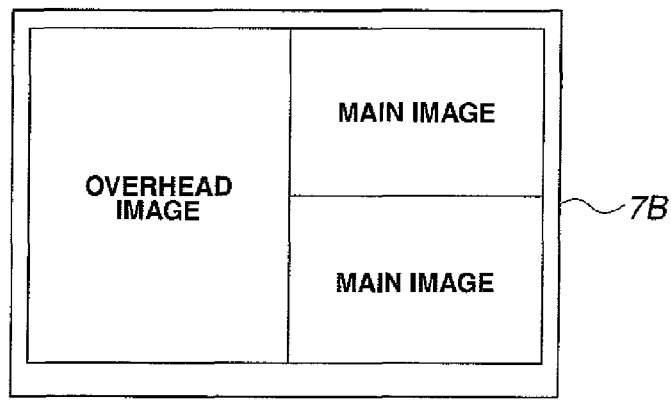
FIG. 12C is a diagram showing a state in which an overhead image and two main images are displayed on one monitor.

One monitor 7B may be provided instead of the overhead monitor 7 and the main monitor 8. In this case, the monitor 7B may be divided into two as shown in FIG. 12B to display an overhead image and a main image of selected one main camera. As shown in FIG. 12C, a main image display area in FIG. 12B may be further divided into two to simultaneously display two main images.

Figure 12D:
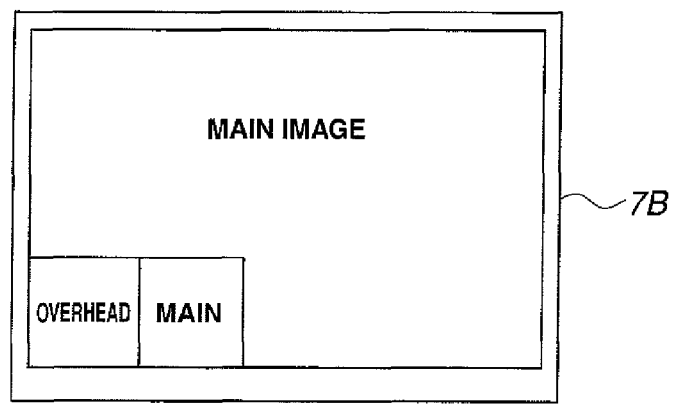
FIG. 12D is a diagram showing a state in which a main image and an overhead image are displayed on one monitor as parent and child images.

As shown in FIG. 12D, an overhead image and a main image may be displayed as parent and child images or one of the overhead image and the main image may be displayed as a reduced image (a thumbnail image).

In the case of FIG. 12D, for example, a main image by one main camera is shown in a state displayed as a parent image (an unreduced image), the overhead image is shown in a state displayed as a reduced image, and a main image of the other main camera is shown in a state displayed as a reduced image.

The display of FIG. 12D may be able to be displayed with the parent image and the reduced image interchanged by an image selection switch. A medical apparatus may be configured by one overhead camera 3A and one main camera 4A. In this case, the medical apparatus may be configured to use the overhead monitor 7 and the main monitor 8 or may be configured to use one monitor 7B.

In the case of two monitors, the overhead image and the main image are respectively displayed on the monitors. On the other hand, in the case of the one monitor 7B, the overhead image and the main image may be displayed as shown in FIG. 12B. The main image and the overhead image may be displayed as parent and child images similar to those shown in FIG. 12D.

Image storing means for storing an overhead image and a main image as thumbnail images and thumbnail display means for displaying the thumbnail images may be provided. The thumbnail images may be recorded (stored) in time series or may be recorded only when the surgeon records the thumbnail images.

When an image is recorded, selection of recording as an unreduced image and recording as a reduced image may be able to be performed. A comment may be able to be recorded in association with the image or may be additionally recorded.

As explained above, according to this embodiment, the place PN treated in the past where a predetermined change such as bleeding is likely to occur in an overhead image can be recorded as history information in advance in association with the setting information of the main cameras 4A and 5A that pickup images of the place and can be displayed on the display means. Therefore, when the surgeon recognizes a predetermined change such as bleeding in the treated place PN in the overhead image, there is an effect that the surgeon can easily check the place PN quickly and in detail with simple operation.

In the first embodiment explained above, when a situation that the surgeon desires to check such as bleeding occurs in a place treated in the past, the surgeon can perform operation for displaying histories of plural places treated in the past.

On the other hand, as in a modification explained below, when monitoring means for monitoring a predetermined change such as bleeding is provided for places treated in the past to recognize (detect) the predetermined change, the places may be able to be notified to the surgeon. FIG. 13A shows a medical apparatus 1B according to a modification of the first embodiment.

In the medical apparatus 1B, in the processor 6 in the medical apparatus 1 shown in FIG. 1, a change monitoring section 51, as monitoring means for monitoring (recognizing) whether a predetermined change such as bleeding occurs in an image area portion set in a place treated in the past, is provided.

Figure 13B:
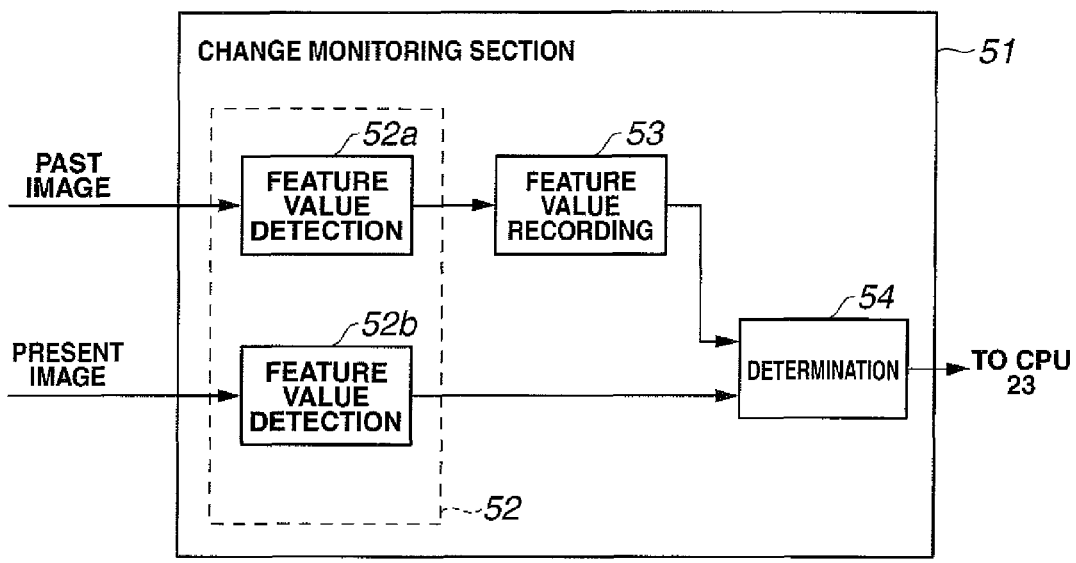
FIG. 13B is a block diagram showing a configuration example of a change monitoring section.

As shown in FIG. 13B, the change monitoring section 51 includes a feature value detecting section 52 that detects (extracts), from a past (overhead) image, a feature value of an image area set in a treated place in the image, a feature value recording section 53 that records the detected past feature value, and a determining section (recognizing section) 54 that sets the feature value as reference image data, compares the feature value with a feature value of image data in the same image area in a future (present) overhead image, and determines (or recognizes) presence or absence of (the occurrence of) a predetermined change.

In this modification, after treatment is performed in places, immediately before a place to be treated is moved, at least images of image areas set in the treated places in an overhead image are recorded in the recording means such as the memory for control 24 as past images. In this case, the images may be recorded according to instruction operation by the surgeon or the movement may be recognized as an image and an image immediately before the movement may be recorded.

In FIG. 13B, the feature value detecting section 52 is configured by a configuration example including the feature value detecting section 52a that detects a feature value from a past image and the feature value detecting section 52b that detects a feature value from a present image. However, one of the feature value detecting sections 52a and 52b may be used in common.

For example, when a present state of treatment shown in FIG. 13A is, for example, treatment performed in the place P3, predetermined image areas R1 and R2 set respectively in the places P1 and P2 in a past overhead image are set.

In FIG. 13A, the image areas R1 and R2 shown on the overhead image indicate a setting example thereof. The image areas R1 and R2 do not always need to be displayed as an image (selection of display may be able to be performed by an option function).

A feature value extracted in the image area R1 of the past place P1 and a feature value extracted in the image area R2 of the past place P2 are recorded in the feature value recording section 53.

The determining section 54 determines whether the past feature values and feature values extracted in the same image areas R1 and R2 in an overhead image acquired at present change by an amount equal to or larger than a threshold set in advance.

When the feature values do not change by an amount equal to or larger than the threshold, the change monitoring section 51 continues the same processing, for example, after a predetermined time interval. On the other hand, when the feature values change by an amount equal to or larger than the threshold, the determining section 54 outputs a determination result to the CPU 23. The CPU 23 displays, for example, a number to be superimposed on a place or an image area corresponding to the determination result in an overhead image displayed at present and informs the surgeon that it is likely that bleeding occurs.

When the surgeon desires to check the place or the image area in more detail according to the information, the surgeon designates the number. The CPU 23 controls to move the main cameras 4A and 5A to pick up images of the place.

As a method of information in this case, the CPU 23 may perform display for requesting the surgeon to confirm whether the surgeon desires to check the place or the image area in more detail or desires to move the main cameras 4A and 5A.

When the surgeon replies that the surgeon desires to check the place or the image area in more detail or move the main cameras 4A and 5A, the CPU 23 controls to move the main cameras 4A and 5A. On the main monitor 8, a main image by the main camera 4A or 5A is displayed and the surgeon can check the main image in detail.

Figure 13C:
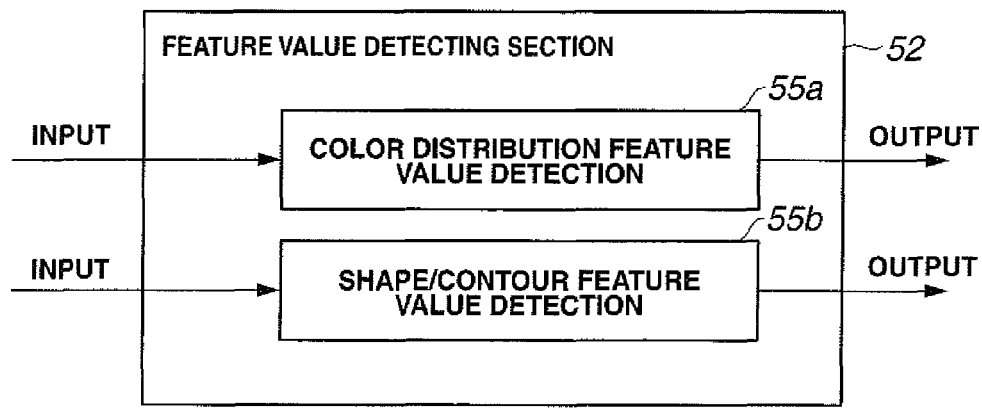
FIG. 13C is a block diagram showing a configuration example of a feature value detecting section.

The feature value detecting section 52 (shown in the case in which the feature value detecting section 52a or 52b is used in common) includes a color distribution feature value detecting section 55a that detects a color distribution of an image of an image area as a feature value, for example, as shown in FIG. 13C and a shape/contour feature value detecting section 55b that detects a shape or a contour of the image of the image area as a feature value.

The determining section 54 compares the feature values and determines presence or absence of a predetermined change such as bleeding. For example, when a place treated and recorded in the past bleeds, a color distribution characteristic of red increases to correspond to the bleeding. Therefore, the determining section 54 can easily determine from a detection output of the color distribution feature value detecting section 55a that the place bleeds.

When a shape or a contour of a bleeding portion changes, the shape/contour feature value detecting section 55b detects the change. The determining section 54 determines from an output of the detection that the portion bleeds.

According to this modification, from a predetermined image area in a treated place in a past overhead image recorded on the processor 6 side of the medical apparatus 1B, a feature value of the image area is extracted and recorded, it is monitored whether the feature value temporally changes by an amount equal to or larger than a predetermined threshold, and, when the feature value changes by an amount equal to or larger than the predetermined threshold, the surgeon is informed of the place and the like.

Therefore, according to this modification, besides the effects of the first embodiment, the surgeon can more concentratedly treat a place being currently treated and operability for the surgeon can be improved. This modification can provide the medical apparatus 1B in an environment in which the surgeon can easily perform a surgical operation.

In this modification, when the determining section 54 determines that the predetermined change occurs, the CPU 23 may be set to perform control to move one of the two main cameras 4A and 5A such that, for example one of the two main cameras 4A and 5A automatically picks up a place where the change occurs. The surgeon can quickly check, with one main camera, a state in which a predetermined change such as bleeding occurs. According to a check result, the surgeon may perform instruction operation for returning moved one main camera to a state before the movement or perform instruction operation for moving the other main camera in the same manner as one camera.

The first embodiment may be applied to a configuration including one main camera and an endoscope without including the overhead camera 3A. In this case, since an overhead image is not obtained, a place and a number in an overhead image and setting information of an image pickup position by the main camera cannot be associated with each other. However, the surgeon performs operation for image recording to thereby associate, during operation for image recording by the main camera, setting information, a place, and a number with the memory for control 24 of the processor 6 and simultaneously records an hour during the operation.

The surgeon can display a past history of images picked up by the main camera.

Therefore, while the surgeon performs a surgical operation using, for example, the one main camera and the endoscope (a rigid endoscope or a flexible endoscope), when the surgeon recognizes (finds) a predetermined change such as bleeding in a place treated in the past by the endoscope, the surgeon only has to perform operation for displaying a past history in a main image recorded by the main camera.

In reproduced images of a past main image displayed on the main monitor 8, the surgeon specifies a place (or a number) of a reproduced image corresponding to the place where the predetermined change is recognized by the endoscope. The surgeon only has to perform instruction operation to move the main camera to the place of the number.

Then, the main camera quickly moves to the place where the surgeon recognizes the bleeding or the like and displays a picked-up image on the main monitor 8. Therefore, the surgeon can recognize a state of the bleeding or the like in detail.

The modification is explained in the case of one main camera and the endoscope. However, the modification can be applied in the same manner in a case of two main cameras and an endoscope.

Second Embodiment

Figure 14:
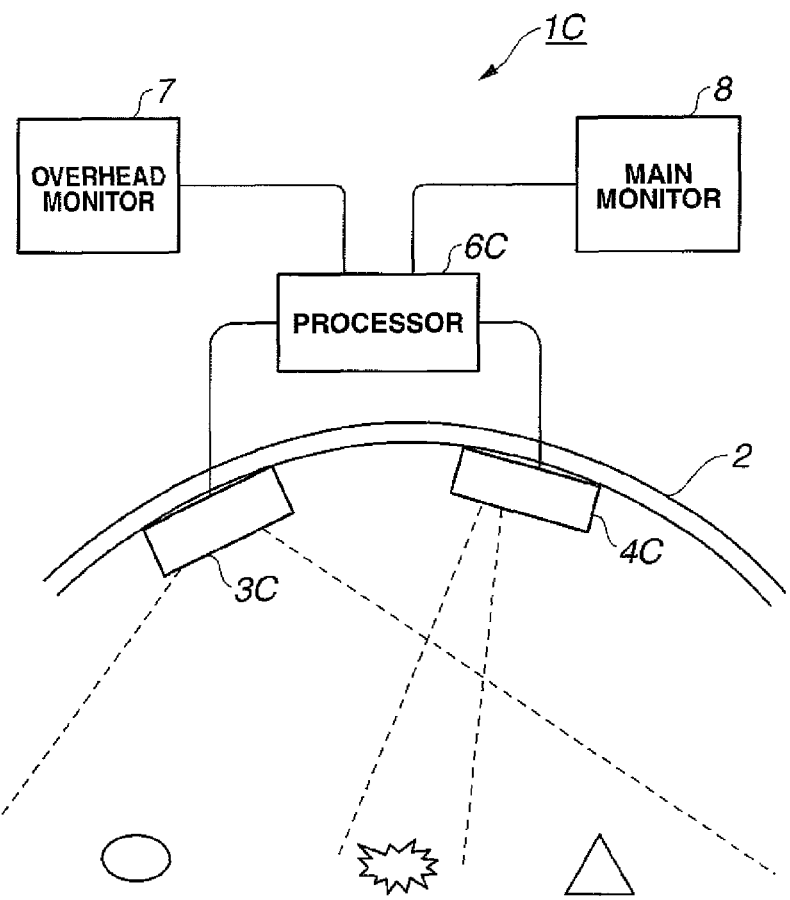
FIG. 14 is an overall configuration diagram of a medical apparatus according to a modification of a second embodiment of the present invention.

FIG. 14 shows a medical apparatus 1C according to a second embodiment of the present invention. The medical apparatus 1C according to this embodiment includes an overhead camera 3C that picks up an image of an entire inside of an abdominal cavity at a wide angle and a main camera 4C that observes the inside of the abdominal cavity in enlargement, the overhead camera 3C and the main camera 4C being fixed to an abdominal wall of the abdomen 2, a processor 6C, an overhead monitor 7 that displays an overhead image by the overhead camera 3C, the main monitor 8 that displays a main image by the main camera 4C, and a not-shown camera operation I/F.

The processor 6C is configured to perform transmission of a signal between the overhead camera 3C and the main camera 4C by wire in the processor 6 according to the first embodiment or the processor 6B according to the modification. Further, this embodiment includes functions explained below.

Figure 15:
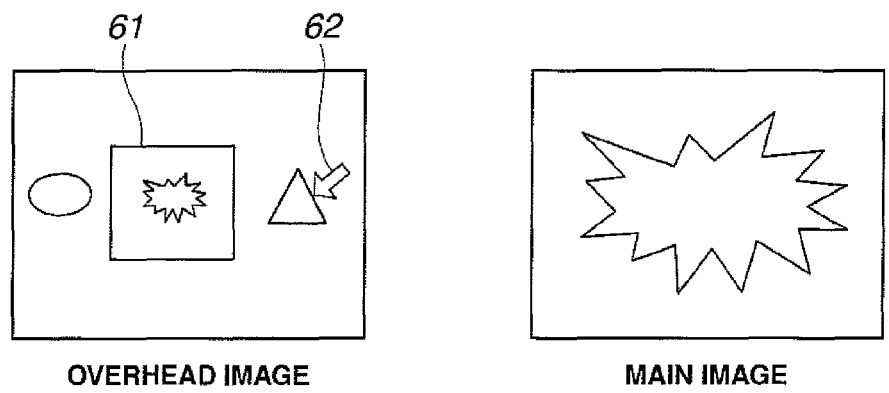
FIG. 15 is a diagram showing displayed images on an overhead monitor and a main monitor.

FIG. 15 shows display images of the overhead monitor 7 and the main monitor 8. In an overhead image, an enlarged image display range frame (hereinafter simply referred to as display frame) serving as a mark 61 for always showing which part the main camera 4C projects. For this purpose, six-axis sensors are mounted on the cameras 3C and 4C. The processor 6B can always grasp an image pickup position and an image pickup direction.

When a place desired to be observed in enlargement on an overhead image is clicked with a cursor 62, the main camera 4C moves to display the clicked place. The place is displayed in enlargement as shown on a right side of FIG. 15. The display range frame serving as the mark 61 moves according to the movement of the main camera 4C.

When, for example, a right click of a mouse as operating means for the cursor 62 is continued, enlargement magnification of the main camera 4C increases. When a left click is continued, the enlargement magnification decreases.

The main camera 4C can measure a distance between the main camera 4C and a surface 65 of a treatment target organ (place) according to a following procedure by emitting infrared rays from infrared ray emitting sections 64a and 64b provided at both ends of the main camera 4C.

Figure 16:
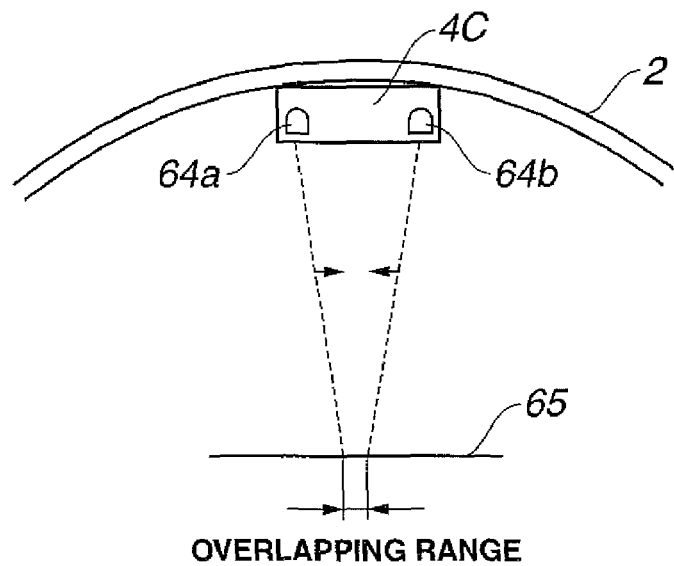
FIG. 16 is an explanatory diagram of a state in which infrared rays are emitted from both ends of a main camera.

As shown in FIG. 16, 1) the infrared rays are emitted from both the ends of the main camera 4C along a field of view direction of the main camera 4C to an inner side in the field of view direction.

Figure 17:
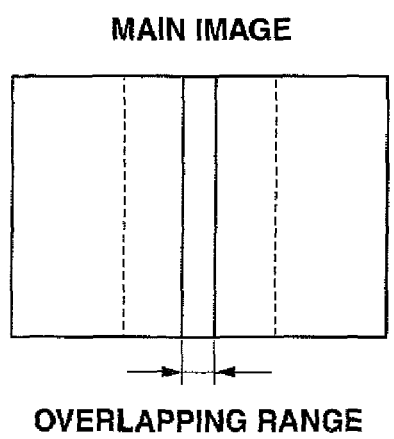
FIG. 17 is an explanatory diagram of calculation of a distance from overlap of the infrared rays.

An overlapping range of the emitted infrared rays increases according to a distance from the main camera 4C. Therefore, as shown in FIG. 17, 2) positions of the infrared rays are grasped on a screen of a main image and the distance is calculated from a tilt of the infrared ray emission in an overlapping position.

In this embodiment, an inside of an abdominal cavity can be observed through an overhead image and a display range of an enlarged observation image by the main camera 4C is always superimposed on the overhead image. Therefore, a user such as a surgeon can grasp more easily than in the past which part of the entire inside of the abdominal cavity the user is observing.

Simply by clicking a place desired to be observed in enlargement on the overhead image, the main camera 4C automatically moves and can display the target place. An image that the surgeon desires to obtain can be displayed more conveniently and quickly than in the past.

Third Embodiment

Figure 18:
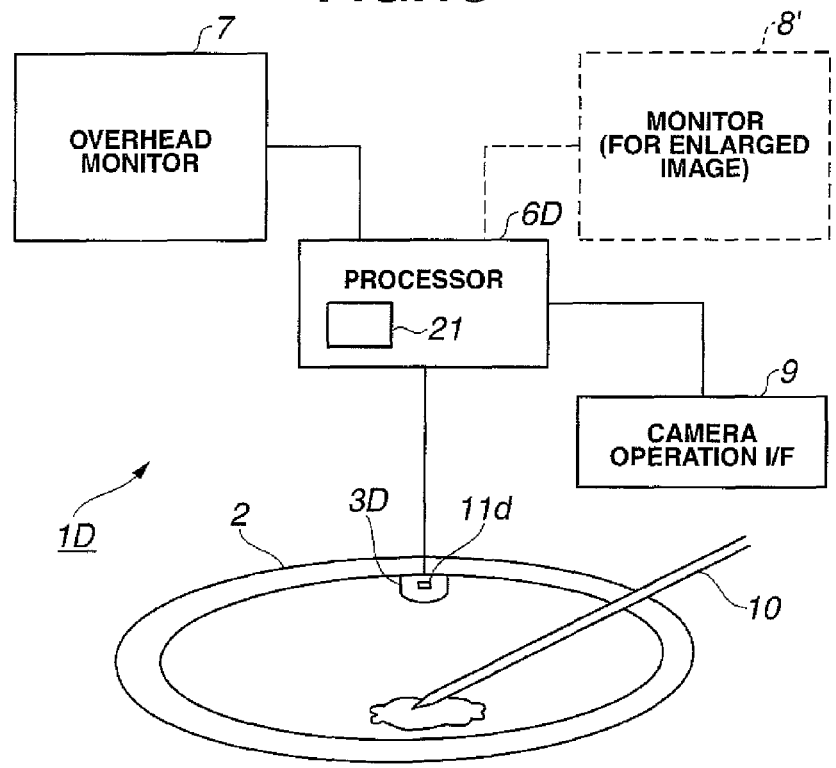
FIG. 18 is a configuration diagram showing an overall configuration of a medical system according to a third embodiment of the present invention.

FIG. 18 shows a medical apparatus 1D according to a third embodiment of the present invention. The medical apparatus 1D according to this embodiment includes an overhead camera 3D that is fixed to an abdominal wall of the abdomen 2 and picks up an image of an entire inside of an abdominal cavity at a wide angle, a processor 6D that performs image processing and the like for the overhead camera 3D, the overhead monitor 7 that displays an overhead image by the overhead camera 3D, and the camera operation I/F 9. Besides the overhead monitor 7, a monitor (for an enlarged image) 8' (indicated by a dotted line) that displays an enlarged image by electronic zoom may be provided. The overhead camera 3D and the processor 6D are shown as a configuration for performing transmission of a signal by wire but may be configured to perform transmission of a signal by radio.

The overhead camera 3D includes an image pickup unit 11d including a high-resolution image pickup element. The image pickup unit 11d picks up an entire inside of an abdominal cavity at a wide angle. The processor 6D includes a processing function for applying area selection to an overhead image picked up by the image pickup unit 11d through operation of the camera operation I/F 9 and displaying an area selected by the area selection in enlargement through electronic zoom.

Figure 19A:
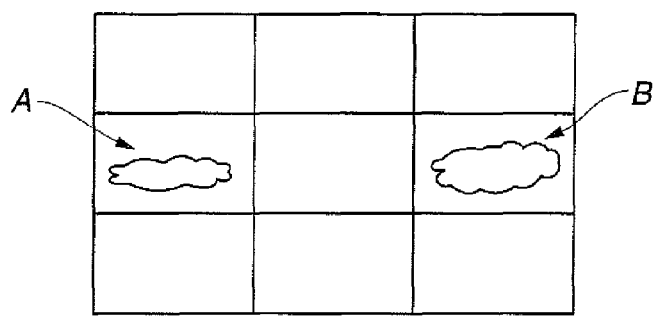
FIG. 19A is a diagram showing an overhead image example displayed on an overhead monitor.
Figure 19B:
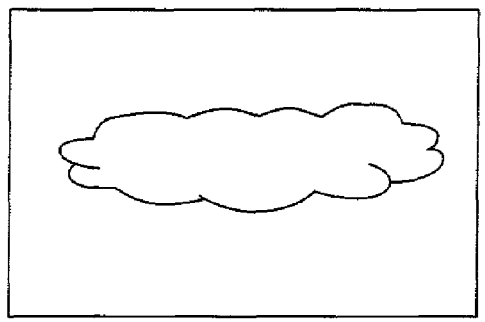

For example, FIG. 19A shows an overhead image displayed on the overhead monitor 7 in a state in which the electronic zoom is not performed. In the overhead image, images of a place A and a place B as two area explained later are included. FIG. 19B shows an enlarged image in which the place B as a selected area is displayed in enlargement by the electronic zoom. When the monitor 8' is provided, the enlarged image is displayed on the monitor 8'. When only one overhead monitor 7 is provided, the enlarged image is displayed on the overhead monitor 7.

This embodiment is configured to realize, with the high-resolution overhead camera 3D, both a function of an overhead camera that surveys the entire inside of the abdominal cavity and a function similar to the function of the main camera, an image pickup position of which is moved, explained above in the embodiments.

The processor 6D incorporates the image processing unit 21 including the change monitoring section 51 explained with reference to FIG. 13A. The surgeon can apply treatment to a treatment target region in the abdominal cavity with the treatment instrument 10 while observing an overhead image. The processor 6D includes the memory for control 24 and the video signal output unit 25 in FIG. 13A.

Operations in this embodiment are explained with reference to FIG. 20.

In first step S1, an image of the entire inside of the abdominal cavity is picked up by the overhead camera 3D. The processor 6D displays an overhead image on the overhead monitor 7. A display example of the overhead image is, for example, as shown in FIG. 19A. The surgeon can grasp a state of the entire inside of the abdominal cavity by observing the overhead image.

As shown in step S2, in order to treat the place A, the surgeon selects the place A through operation of area selection of the camera operation I/F 9 to make it possible to observe the place A in more detail in the overhead image shown in FIG. 19A.

According to the operation of area selection in step S2, as shown in step S3, area information of the selected place A is recorded in the processor 6D. As shown in step S4, the processor 6D applies processing of electronic zoom for enlarging an image of the place A part to the selected place A. As shown in FIG. 19B, the image part of the place A is displayed in enlargement.

The surgeon starts treatment using the treatment instrument 10 as shown in step S5 while observing the enlarged image. Thereafter, when the surgeon ends the treatment, as shown in step S6, the electronic zoom is stopped. As in the case of step S1, an overhead image obtained by picking up an image of the entire inside of the abdominal cavity is displayed on the overhead monitor 7.

As shown in step S7, the change monitoring section 51 in the processor 6D records an image (for which the treatment ends) of the place A as a past image and records a feature value of the image (as a reference feature value used for determination of a change).

Thereafter, as shown in step S8, the change monitoring section 51 acquires a feature value of the place A at every predetermined time interval, compares the feature value with the reference feature value, and determines (recognizes) presence or absence of a predetermined change.

In determining presence or absence of a predetermined change, as explained with reference to FIG. 13C, the change monitoring section 51 determines whether, for example, a feature value of a color distribution by the color distribution feature value detecting section 55a and a feature value of a shape or a contour by the shape/contour feature value detecting section 55b change by an amount equal to or larger than a threshold set in advance.

In this case, to make the determination less susceptible to an influence due to a periphery of the place A to be determined, for example, concerning a designated color, a temporal spread of a range or an area of the color may be detected. Determination processing for presence or absence of a change at the predetermined time interval in FIG. 8 is shown in step S9.

In the case of a determination result indicating absence of the predetermined change in step S9, the surgeon continues a surgical operation. For example, when the surgeon attempts to treat another place B different from the place A (according to the same operation as that in the case of step S2), in step S10, the surgeon performs area selection, i.e., selects the place B in the overhead image shown in FIG. 19A.

According to the operation for area selection in step S10, as shown in step S11, the processor 6D records area information of the selected place B. As shown in step S12, the processor 6D applies processing of electronic zoom for enlarging an image of the place B part to the selected place B.

The surgeon starts treatment using the treatment instrument 10 as shown in step S13 while observing the enlarged image. Thereafter, when surgeon ends the treatment as shown in step S14, the electronic zoom is stopped. As in the case of step S1, an overhead image obtained by picking up an image of the entire inside of the abdominal cavity is displayed on the overhead monitor 7.

When treatment of another place (a place C) is further performed, the processing in step S7 and subsequent step is performed in the same manner (however, the place A in step S7 is read as the place B and the place B in step S10 is read as the place C).

Figure 20:
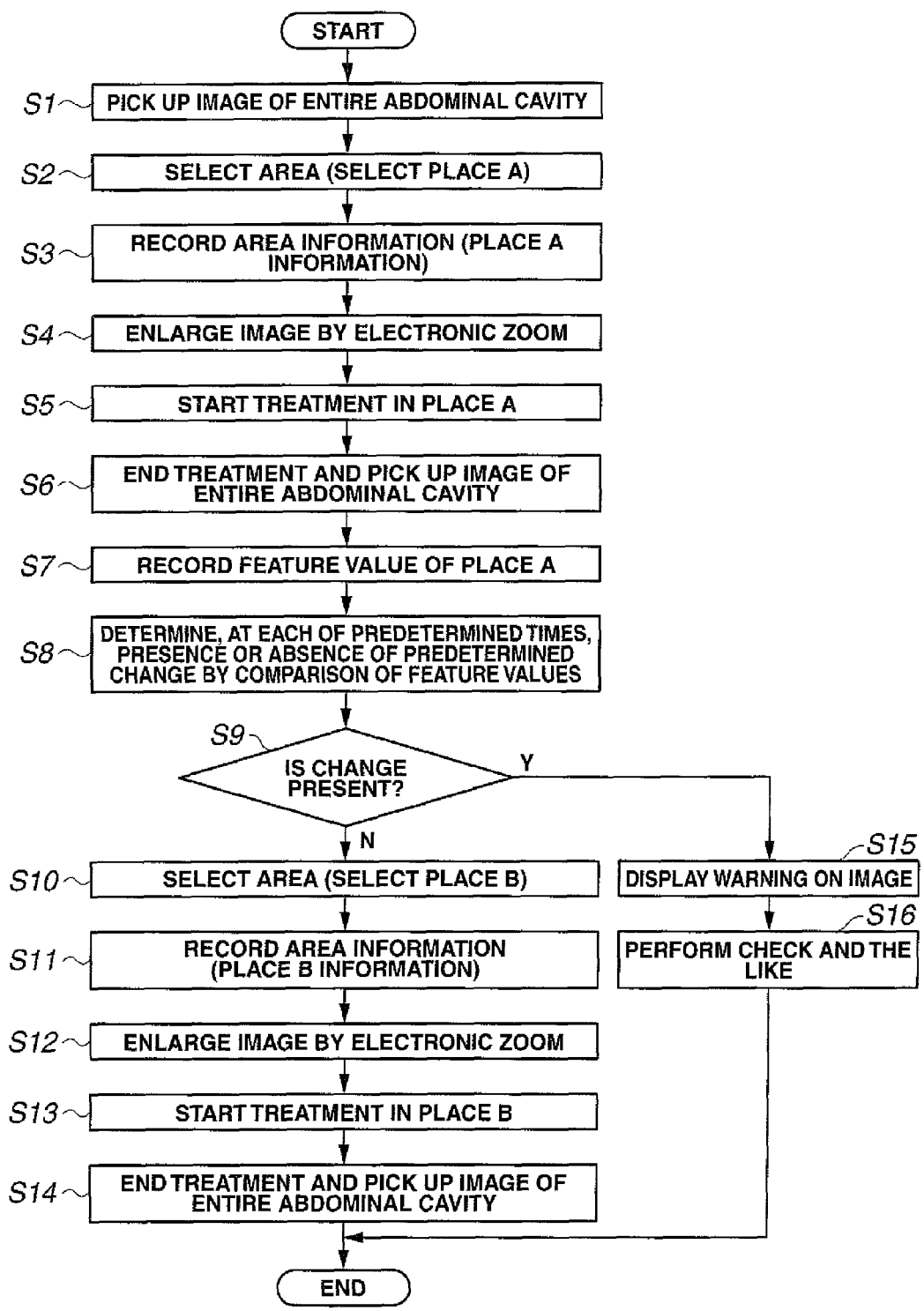
FIG. 20 is a flowchart showing representative processing contents according to the third embodiment.

On the other hand, after the treatment of the place B in step S14, when the surgeon attempts to end the surgical operation, the surgeon ends the processing shown in FIG. 20.

In the case of a determination result indicating presence of a change in the determination processing in step S9, as shown in step S15, the processor 6D displays warning information (or notice information) indicating presence of a change on the overhead monitor 7. Specifically, the processor 6D displays warning information indicating that a change such as bleeding from a state immediately after the treatment is present in the place A.

The surgeon performs a check or the like corresponding to the warning information as shown in step S16. The surgeon can check a state of the place A in response to the warning information and, when treatment is necessary according to a check result, quickly perform the treatment. When treatment is unnecessary, the surgeon can check the unnecessity of treatment. After the processing in step S16, the surgeon ends the processing shown in FIG. 20.

According to this embodiment for performing such operations, since the overhead camera 3D including the high-resolution image pickup element 11d is used, effects substantially the same as those in the case of the modification of the first embodiment can be obtained.

In this embodiment, an overhead image and an enlarged image obtained by enlarging a part of the overhead image can be displayed by one camera (image pickup means) including one high-resolution image pickup unit 11d. Therefore, a surgical operation can be smoothly performed with work simpler than work performed when plural cameras are set in a body cavity.

Fourth Embodiment

Figure 21:
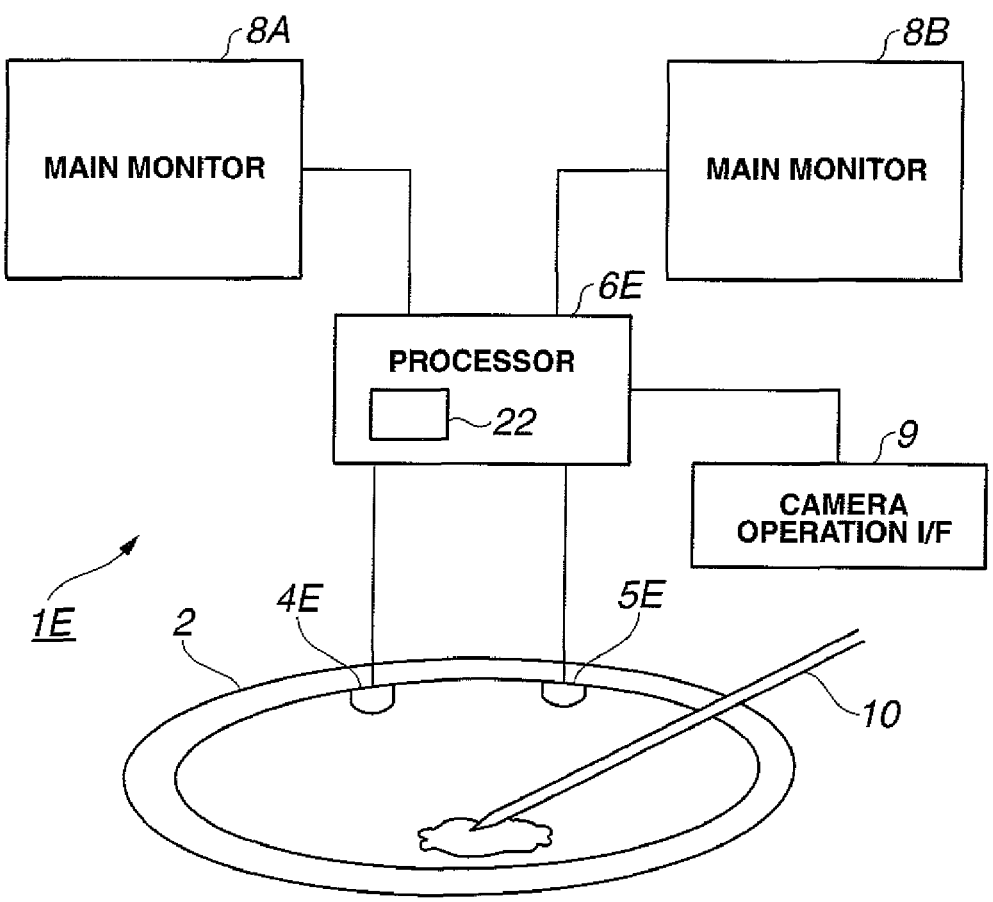
FIG. 21 is a configuration diagram showing an overall configuration of a medical system according to a fourth embodiment of the present invention.

FIG. 21 shows a medical apparatus 1E according to a fourth embodiment of the present invention. The medical apparatus 1E according to this embodiment includes first and second main cameras 4E and 5E that are fixed on the abdominal wall of the abdomen 2 and pick up images of an inside of an abdominal cavity respectively at narrow angles, a processor 6E, main monitors 8A and 8B that respectively display main images by the first and second main cameras 4E and 5E, and the camera operation I/F 9. In FIG. 21, the medical apparatus 1E is shown in a configuration example for performing transmission of a signal by wire.

The first and second main cameras 4E and 5E are image pickup means for enabling change (movement) of an area of which an image is picked up, by pan and tilt and also enabling zoom. For example, the first and second main cameras 4E and 5E can be realized by the same configuration as that of the main cameras 4 and 5 shown in FIG. 13A. Alternatively, the first and second main cameras 4E and 5E may have a structure in which setting positions in the abdominal cavity of the main cameras 4E and 5E can be moved. In this case, the functions of pan and tile are not always necessary.

At least one of the main cameras 4E and 5E can be set in a state of a considerably wide angle when zoom is set to minimum magnification. In other words, one main camera has a function close to an overhead camera.

One main camera can set an image pickup area of the other main camera in an image pickup area of one main camera and grasp the image pickup area of the other main camera.

The processor 6E incorporates the image processing unit 22, the CPU for camera driving control 23, the memory for control 24, and the video signal output unit 25. The image processing unit 22 shown in FIG. 21 includes the change monitoring section 51 explained with reference to FIG. 13A.

In this embodiment, grasp of position information between the two main cameras 4E and 5E can be performed by the method explained with reference to FIGS. 7 to 11 above.

This embodiment is a configuration example having functions similar to those in the third embodiment using the two main cameras 4E and 5E.

Figure 22:
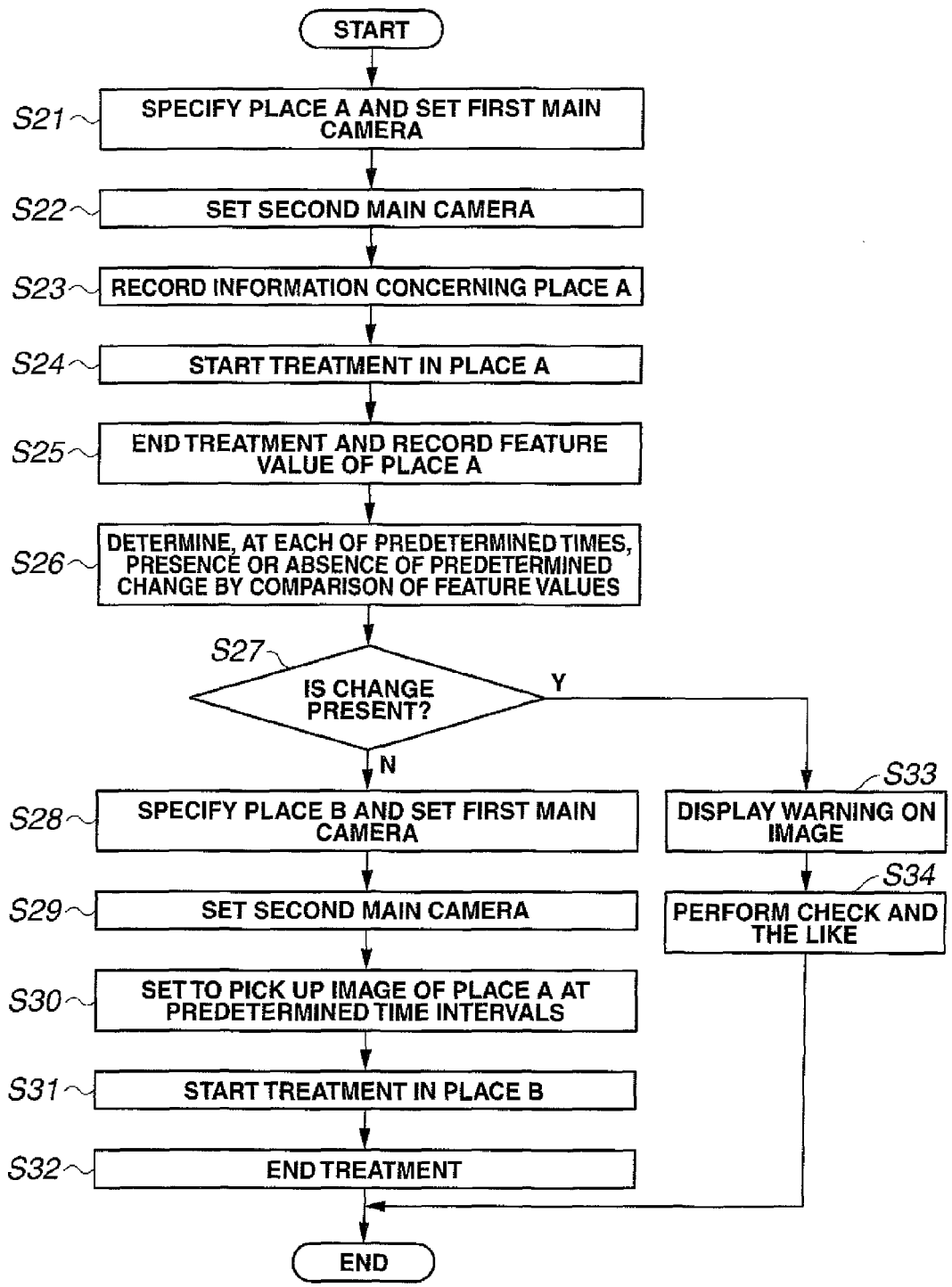
FIG. 22 is a flowchart showing representative processing contents according to the fourth embodiment.

A representative operation example according to this embodiment is explained with reference to a flowchart of FIG. 22.

In first step S21, the surgeon specifies an area (the place A) where the first main camera 4E is intended to be set and sets the area as an image pickup area of which an image is picked up. In other words, the surgeon moves and sets the main camera 4E and performs setting of pan, tilt, and the like such that the main camera 4E can pick up an image of the place A to be treated.

In step S22, concerning the second main camera 5E, the surgeon also sets the place A to be treated to be included in an image pickup area.

Besides the method in which the surgeon performs the setting of the main camera 5E, the setting of the main camera 5E may be automatically performed using, for example, relative position information with the main camera 4E and shape recognition for an object such as the distal end portion of the treatment instrument 10 set in the place A to be treated.

In next step S23, the processor 6E records area information (information concerning the place A) of the main cameras 4E and 5E.

In next step S24, the surgeon starts treatment using the treatment instrument 10 in the place A. In this case, the surgeon performs the treatment while observing main images picked up by the main cameras 4E and 5E. Then, the surgeon ends the treatment in the place A.

In step S25, the processor 6E records an image of the place A, for which the treatment ends, as a past image. The change monitoring section 51 records a feature value of the place A as a reference feature value.

In the next step S26, the change monitoring section 51 acquires a feature value of the place A at every predetermined time interval, compares the feature value with the reference feature value, and determines (recognizes) presence or absence of a predetermined change.

In determining presence or absence of a predetermined change, as explained with reference to FIG. 13C, the change monitoring section 51 determines whether, for example, a feature value of a color distribution by the color distribution feature value detecting section 55a and a feature value of a shape or a contour by the shape/contour feature value detecting section 55b change by an amount equal to or larger than a threshold set in advance. Determination processing for presence or absence of a change at the predetermined time interval in FIG. 22 is shown in step S27.

In the case of a determination result indicating absence of the predetermined change in step S27, the surgeon continues a surgical operation. For example, when the surgeon attempts to treat another place B different from the place A, in step S28, the surgeon specifies the place B and sets the main camera 4E to pick up an image of the place B. A main image by the main camera 4E is displayed on the main monitor 8A.

In step S29, the surgeon sets the main camera 5E to pickup an image of the place B. A main image by the main camera 5E is displayed on the main monitor 8B. In step S30, the main camera 5E is set in a state in which the main camera 5E picks up an image of the place A at a predetermined time interval.

The surgeon starts treatment using the treatment instrument 10 as shown in step S31 while observing the main image. Thereafter, the surgeon ends the treatment, as shown in step S32.

On the other hand, in the case of a determination result indicating presence of a change in the determination processing in step S27, as shown in step S33, the processor 6E displays warning information (or notice information) indicating presence of a change on the overhead monitor 8A or the like.

The surgeon performs a check or the like corresponding to the warning information as shown in step S34. The surgeon can check a state of the place A in response to the warning information and, when treatment is necessary according to a check result, quickly perform the treatment. When treatment is unnecessary, the surgeon can check the unnecessity of treatment. After the processing in step S34, the surgeon ends the processing shown in FIG. 22.

According to this embodiment for performing such operations, effects substantially the same as those in the modification of the first embodiment can be obtained. In this case, the effects substantially the same as those in the modification of the first embodiment can be obtained by using two cameras (image pickup means). Therefore, the surgeon can smoothly perform a surgical operation with simple work.

Embodiments configured by, for example, partially combining the embodiments explained above and the like also belong to the present invention.

What is claimed is:

1. A medical apparatus comprising:
a first image pickup section that is fixed to a body wall and picks up an image of an inside of a body cavity;
a recording section that records in advance, in preparation for a case in which a predetermined image change occurs in a first image picked up by the first image pickup section, a predetermined image area in the first image or a coordinate for specifying the predetermined image area; and
a display section that displays, when the predetermined image change occurs in the first image, the image area or the coordinate recorded in the recording section to be superimposed on the first image picked up by the first image pickup section,
wherein the first image pickup section is an image pickup section that picks up an image of the inside of the body cavity at a wide angle,
the medical apparatus further comprises a second image pickup section that picks up an image of the inside of the body cavity at an angle narrower than the angle of the first image pickup section and an information acquiring section configured to acquire predetermined image pickup position information and image pickup direction information in the second image pickup section, and
in recording a picked-up image picked up by the second image pickup section and the image pickup position information and the image pickup direction information in advance in preparation for the case in which the predetermined image change occurs in the first image, the recording section records the picked up image by the second image pickup section, the image pickup position information, and the image pickup direction information in association with the image area or the coordinate in a state which the image area or the coordinate is set in an image position whose image is picked up by the second image pickup section.

2. The medical apparatus according to claim 1, further comprising a movement control section that moves the second image pickup section on the basis of the image pickup position information and the image pickup direction information recorded in the recording section.

3. The medical apparatus according to claim 2, wherein the movement control section controls movement of the second image pickup section according to a selection instruction for the image area or the coordinate recorded in the recording section, on the first image displayed in the display section.

4. The medical apparatus according to claim 2, wherein the movement control section increases image pickup magnification of the second image pickup section according to a selection instruction for the image area or the coordinate recorded in the recording section, on the first image displayed in the display section.

5. The medical apparatus according to claim 2, further comprising a treatment instrument for performing treatment in an image pickup range of the first image pickup section, wherein
the medical apparatus records a picked-up image picked up by the second image pickup section of a place treated by the treatment instrument in the recording section in association with the image pickup area or the coordinate.

6. The medical apparatus according to claim 1, wherein the display section dividedly displays, on one screen, the first image picked up by the first image pickup section and the picked-up image picked up by the second image pickup section.

7. The medical apparatus according to claim 1, wherein the display section displays in reduction, on one screen, one of the first image picked up by the first image pickup section and the picked-up image picked up by the second image pickup section.

8. A medical apparatus comprising:
a first image pickup section that is fixed to a body wall and picks up an image of an inside of a body cavity;
a recording section that records in advance, in preparation for a case in which a predetermined image change occurs in a first image picked up by the first image pickup section, a predetermined image area in the first image or a coordinate for specifying the predetermined image area; and
a display section that displays, when the predetermined image change occurs in the first image, the image area or the coordinate recorded in the recording section to be superimposed on the first image picked up by the first image pickup section,
wherein the first image pickup section is an image pickup section that picks up an image of the inside of the body cavity at a wide angle,
the medical apparatus further comprises a second image pickup section that picks up an image of the inside of the body cavity at an angle narrower than the angle of the first image pickup section and an information acquiring section configured to acquire predetermined image pickup position information and image pickup direction information in the second image pickup section,
the recording section records, in preparation for the case in which the predetermined image change occurs, a picked-up image picked up by the second image pickup section and the image pickup position information and the image pickup direction information in association with the image pickup area or the coordinate, and when instruction operation for displaying the image area or the coordinate to be superimposed on the first image picked up by the first image pickup section is performed, the medical apparatus displays past history information of the image area or the coordinate recorded in the recording section before the instruction operation.

9. A medical apparatus comprising:

a first image pickup section that is fixed to a body wall and picks up an image of an inside of a body cavity;

a recording section that records in advance, in preparation for a case in which a predetermined image change occurs in a first image picked up by the first image pickup section, a predetermined image area in the first image or a coordinate for specifying the predetermined image area;

a display section that displays, when the predetermined image change occurs in the first image, the image area or the coordinate recorded in the recording section to be superimposed on the first image picked up by the first image pickup section; and a monitoring section that monitors whether, in image information of a present image area corresponding to a past image area recorded in the recording section, the predetermined image change from image information of the past image area occurs, wherein the first image pickup section is an image pickup section that picks up an image of the inside of the body cavity at a wide angle, the medical apparatus further comprises a second image pickup section that picks up an image of the inside of the body cavity at an angle narrower than the angle of the first image pickup section and an information acquiring section configured to acquire predetermined image pickup position information and image pickup direction information in the second image pickup section, and the recording section records, in preparation for the case in which the predetermined image change occurs, a picked-up image picked up by the second image pickup section and the image pickup position information and the image pickup direction information in association with the image pickup area or the coordinate.

10. The medical apparatus according to claim 5, further comprising a monitoring section that monitors whether, in image information of a present image area corresponding to a past image area recorded in the recording section, the predetermined image change from image information of the past image area occurs.

11. The medical apparatus according to claim 10, wherein the monitoring section includes a monitoring section that monitors whether bleeding equal to or larger than a predetermined value occurs as the predetermined image change.

12. The medical apparatus according to claim 9, wherein, when the monitoring section determines that the predetermined image change occurs, the monitoring section performs control to move the second image pickup section such that the second image pickup section picks up an image of an image area where it is determined that the predetermined image change occurs.

13. The medical apparatus according to claim 11, wherein, when the monitoring section determines that the predetermined image change occurs, the monitoring section performs control to move the second image pickup section such that the second image pickup section picks up an image of an image area where it is determined that the predetermined image change occurs.

14. The medical apparatus according to claim 12, wherein, when the monitoring section determines that bleeding equal to or larger than a predetermined value occurs as the predetermined image change from the image information of the past image area recorded in the recording section at an end of treatment of a treatment instrument for performing the treatment, the monitoring section performs control to move the second image pickup section such that the second image pickup section picks up an image of an image area where it is determined that the bleeding occurs.

15. The medical apparatus according to claim 9, wherein the monitoring section includes a feature value detecting section that detects a first feature value of an image of the past image area and a second feature value of an image of the present image area and a determining section that compares the first feature value and the second feature value and determines occurrence of the predetermined image change.

16. The medical apparatus according to claim 9, wherein the monitoring section includes a feature value detecting section that detects a first feature value of an image of the past image area and a second feature value of an image of the present image area and a determining section that compares the first feature value and the second feature value and determines occurrence of bleeding as the predetermined image change.

17. The medical apparatus according to claim 15, wherein the feature value detecting section includes a color distribution feature value detecting section that detects a color distribution feature value in an image of the past image area and a color distribution feature value in an image of the present image area or a shape/contour feature value detecting section that detects a feature value of a shape or a contour in the image of the past image area and a feature value of a shape or a contour in the image of the present image area.

18. The medical apparatus according to claim 16, wherein the feature value detecting section includes a color distribution feature value detecting section that detects a color distribution feature value in an image of the past image area and a color distribution feature value in an image of the present image area or a shape/contour feature value detecting section that detects a feature value of a shape or a contour in the image of the past image area and a feature value of a shape or a contour in the image of the present image area.

* * * * *